United States Patent [19]

Shiraishi et al.

[11] Patent Number: 5,156,053
[45] Date of Patent: Oct. 20, 1992

[54] MEASURING SYSTEM USING A ROBOT

[75] Inventors: Mitsuru Shiraishi, Kawasaki; Hideo Kato, Atsugi, both of Japan

[73] Assignee: Fujitsu Limited, Kawasaki, Japan

[21] Appl. No.: 656,060

[22] PCT Filed: Jun. 19, 1990

[86] PCT No.: PCT/JP90/00800

§ 371 Date: Feb. 19, 1991

§ 102(e) Date: Feb. 19, 1991

[87] PCT Pub. No.: WO90/15982

PCT Pub. Date: Dec. 27, 1990

[30] Foreign Application Priority Data

| Jun. 20, 1989 | [JP] | Japan | 1-155681 |
| Sep. 5, 1989 | [JP] | Japan | 1-230097 |
| Sep. 12, 1989 | [JP] | Japan | 1-235917 |
| Oct. 30, 1989 | [JP] | Japan | 1-279772 |
| Oct. 30, 1989 | [JP] | Japan | 1-279773 |
| Nov. 18, 1989 | [JP] | Japan | 1-298767 |
| Feb. 2, 1990 | [JP] | Japan | 2-23879 |
| Mar. 2, 1990 | [JP] | Japan | 2-52025 |

[51] Int. Cl.$^5$ ............................................. G01N 3/20
[52] U.S. Cl. ............................................. 73/849
[58] Field of Search .......... 73/82, 789, 790, 800, 73/822, 823, 849, 854; 364/506

[56] References Cited

U.S. PATENT DOCUMENTS

| 2,283,730 | 5/1942 | Gardner | 73/849 |
| 4,027,531 | 6/1977 | Dawson | 73/854 |
| 4,108,719 | 8/1978 | Olshausen | 73/789 |

FOREIGN PATENT DOCUMENTS

| 0088350 | 5/1985 | Japan | 73/82 |
| 0245137 | 10/1987 | Japan | 73/82 |
| 8800691 | 1/1988 | World Int. Prop. O. | 73/82 |

OTHER PUBLICATIONS

Topper et al., "Fatigue Testing Techniques for Conditions of Biaxial Stress, Stress Concentration, and Pure Bending", J. Mater (USA), vol. 6, No. 4, Dec. 1971.

Primary Examiner—Robert Raevis
Attorney, Agent, or Firm—Nikaido, Marmelstein, Murray & Oram

[57] ABSTRACT

A robot measuring system automatically measures a mechanical characteristics of an object to be measured. The system includes a pressing robot for adding a predetermined pressing force to the object to be measured. An inner force sensor is mounted to one end of the pressing robot and detects strength of the pressing force through a pressing rod. A displacement gauge touches the object and detects a mechanical distortion caused in the object by the pressing force, a sensing robot supports the displacement gauge and moves the displacement gauge to a measuring position. A microprocessor inputs a detection result of the inner force sensor, controls a motion of the pressing robot based on the detection result, and calculates various mechanical characteristics based on a detection result input from the displacement gauge. A memory stores the various mechanical characteristics calculated from the microprocessor. Calculation of the mechanical characteristics of the plastic article is performed by the microprocessor by using a spline smoothing method.

19 Claims, 21 Drawing Sheets

Fig.4

① SET SOKU 0 0 50
② SET STEP 10 0 0
③ MOVE SOKU STEP 3
④ MOVE SOKU STEP
⑤ MOVE SOKU
⑥ LOOP 10
⑦ MOVE SOKU STEP LOOP
⑧ MEASURE
⑨ ENDLOOP

Fig.7A
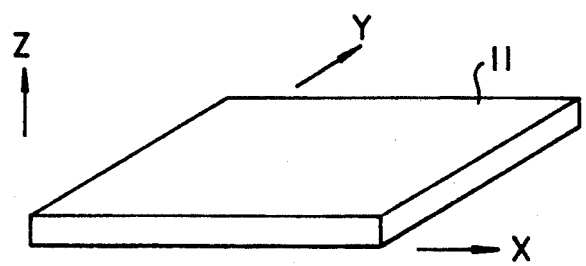
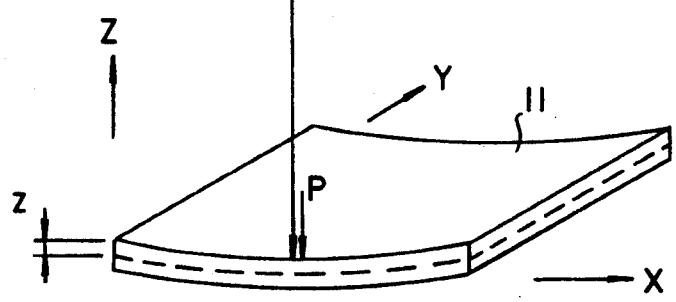
Fig.7B

MEASURING SYSTEM USING A ROBOT

TECHNICAL FIELD

The present invention relates to a measuring system using a robot, particularly, it relates to a robot measuring system which can automatically measure mechanical characteristics of a plastic molded article, for example, displacement, distortion, and stress of the plastic molded article, and distribution characteristic thereof, and then evaluate these characteristics.

BACKGROUND OF THE INVENTION

Plastic molded articles are widely used as bodies of various articles, particularly, electric goods and electronic goods. The plastic molded article, in general, is used in the state which a bending load is added to the plastic molded article. Accordingly, it is necessary to measure the displacement, distortion, and stress when the bending load is added. In this case, since the stress cannot be directly measured, in general, it is measured based on the conversion obtained from the relationship with the distortion.

In general, the basic equation for analyzing the mechanical characteristics of the structure of the molded article is defined by the strength of the materials. According to the strength of the materials, the mechanical characteristic is obtained by the balance of the force, the relationship between the displacement and the distortion, and the relationship between the stress and the distortion in the very small area dA.

The displacement, distortion, stress, and force are important factors in the evaluation of the mechanical characteristics. In this case, the displacement and the distortion are expressed as a geometrical quantity, and the force and the stress are expressed as a dynamic quantity.

In general, the specifications of the plastic molded article are defined by the maximum displacement obtained at the moment when an external force having, for example, an intensity of 1 N (one Newton) is applied to the molded article. That is, the maximum displacement is defined by a predetermined value (for example, below 1 mm) and, the mechanical characteristics are mainly defined by the displacement. Further, the intensity of the molded article is evaluated by the amount of distortion or stress applied by an external force to the molded article. As is known, when stress (distortion) over a predetermined value is applied to the molded article, the molded article is destroyed. The amount of stress (distortion) that can be applied to the molded article varies depending on the material and the structure of the molded article.

Conventionally, there are two methods for evaluating the mechanical characteristic of a plastic molded article. One is a method using the special test piece, and the other is a method using the plastic molded article. The first method is performed by using a small test piece having a predetermined size which is cut off from the molded article. The height, width, and thickness of the test piece is defined by a national standard. The second method is performed based on the predetermined specification as explained above regarding the molded article.

For example, as explained above, the displacement is measured by adding the predetermined pressing force to the test point on the plastic molded article to be tested. Usually, two or three test points are defined on the molded article to shorten the measuring time. Accordingly, in the conventional method, it is very troublesome and difficult to perform measurement by adding the pressing force to various optional points besides the test point, and to quickly measure the displacement at that point.

Further, in the measurement of distortion, in general, a strain gauge is adhered to the molded article to be measured, and a change in the electrical characteristics of the strain gauge is measured before and after adding the pressing force. However, the range of this measurement is limited to only a special measuring point to which the strain gauge is attached. Further, it is troublesome to perform the adhesion and the wiring of the strain gauge so that additional time is required to measure the distortion.

In general, a plastic molded article has characteristics which change in accordance with molding conditions, such as molding temperature, and molding pressure. Accordingly, to obtain the desired characteristics of the molded article, it is necessary to evaluate of the characteristics at optional points based on the conditions of the actual plastic mold. In this case, it is necessary to quickly perform measurement of displacement, distortion, and stress to actually evaluate the deformation state and the added pressing force.

To satisfy the above requirements, the present inventor proposes a robot measuring system which can measures automatically and precisely measure the mechanical characteristics of a plastic molded article in the deformation state when adding the pressing force.

DISCLOSURE OF THE INVENTION

The object of the present invention is to provide a robot measuring system which can automatically, quickly, and precisely measure a mechanical characteristics of a plastic molded article, for example, displacement, distortion, and stress of the plastic molded article, along with distribution characteristics thereof, then evaluate these characteristics.

The robot measuring system according to the present invention, which can automatically measure the mechanical characteristics of an object to be measured, is constituted by: a pressing robot for adding a predetermined pressing force to an object to be measured; a force detection mechanism mounted on the head of the pressing robot through a pressing rod for detecting the intensity of the pressing force; a displacement detection mechanism which touches the object to be measured and detects the mechanical displacement caused by the pressing force in the object; a sensing robot for supporting the displacement detection mechanism and moving the displacement detection mechanism to a measuring point; a microprocessor for inputting a resultant data detected by the force detection mechanism, controlling the motion of the pressing robot based on the resultant data, inputting the resultant data detected by the displacement detection mechanism, and calculating various mechanical characteristics based on the resultant data of the displacement detection mechanism; a memory for storing various mechanical characteristics calculated by the microprocessor; wherein the calculation of the mechanical characteristics is performed based on so-called spline smoothing method.

BRIEF DESCRIPTION OF THE DRAWINGS

FIG. 4 is an illustration showing an example of commands used by an operator for movement and measurement shown in FIG. 3.

FIG. 7A is an illustration for explaining the condition of an object to be measured before deformation occurs.

FIG. 7B is an illustration for explaining the condition an object to be measured after deformation occurs.

BEST MODE EMBODYING THE INVENTION

Figure 1:
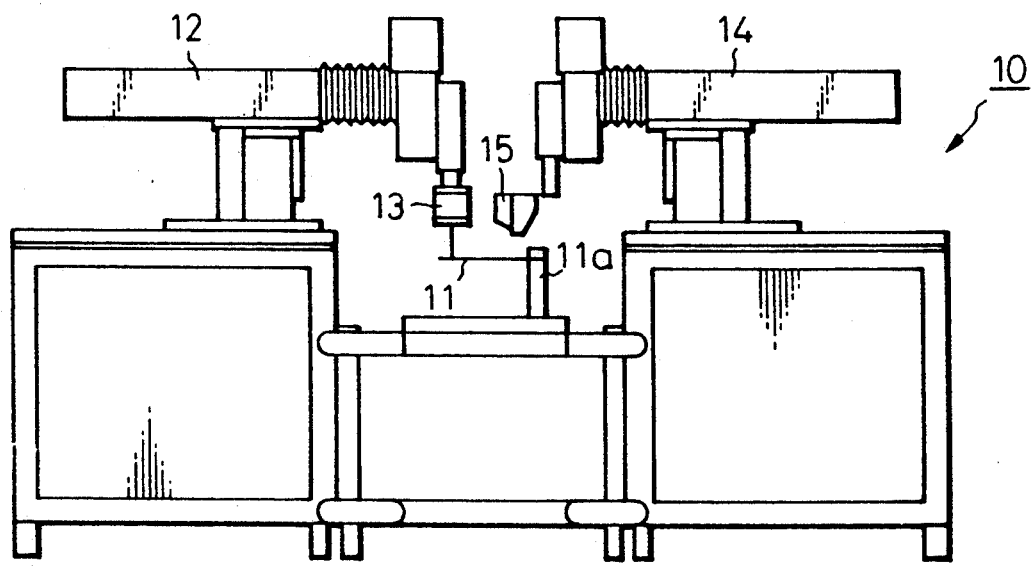
FIG. 1 is an exterior structural view of a robot measuring system according to the present invention.

FIG. 1 is an outside structural view of a robot measuring system according to the present invention. A robot measuring system 10 is provided on a base with two kinds of robots, that is, a pressing robot 12 and a sensing robot 14. A pressing rod is provided on the vicinity of the head of the pressing robot 12 through an inner force sensor 13 contacting with an object to be measured. A displacement gauge 15 is provided adjacent to the head of the sensing robot 14.

The pressing robot 12 forces a pressing rod through the inner force sensor 13 to contact with an optional portion on the object 11, and can give an optional pressing force thereto using a force control. The pressing robot 12 can control a pressing force in the range of 0 to 20 N. The inner force sensor 13 has degrees of freedom of six, and is used for detecting a force added on the pressing rod.

A laser displacement gauge 15 is provided on the head of the sensing robot 14 and can measure the displacement quantity at a resolution of 0.5 μm.

The pressing robot 12 and the sensing robot 14 are rectangular robots having the degrees of freedom of four, X, Y, Z, θ. For example, the sensing robot 14 sequentially measures the displacement of the object 11 by adding a predetermined pressing force via the pressing robot so that the displacement distribution is obtained.

Figure 2:
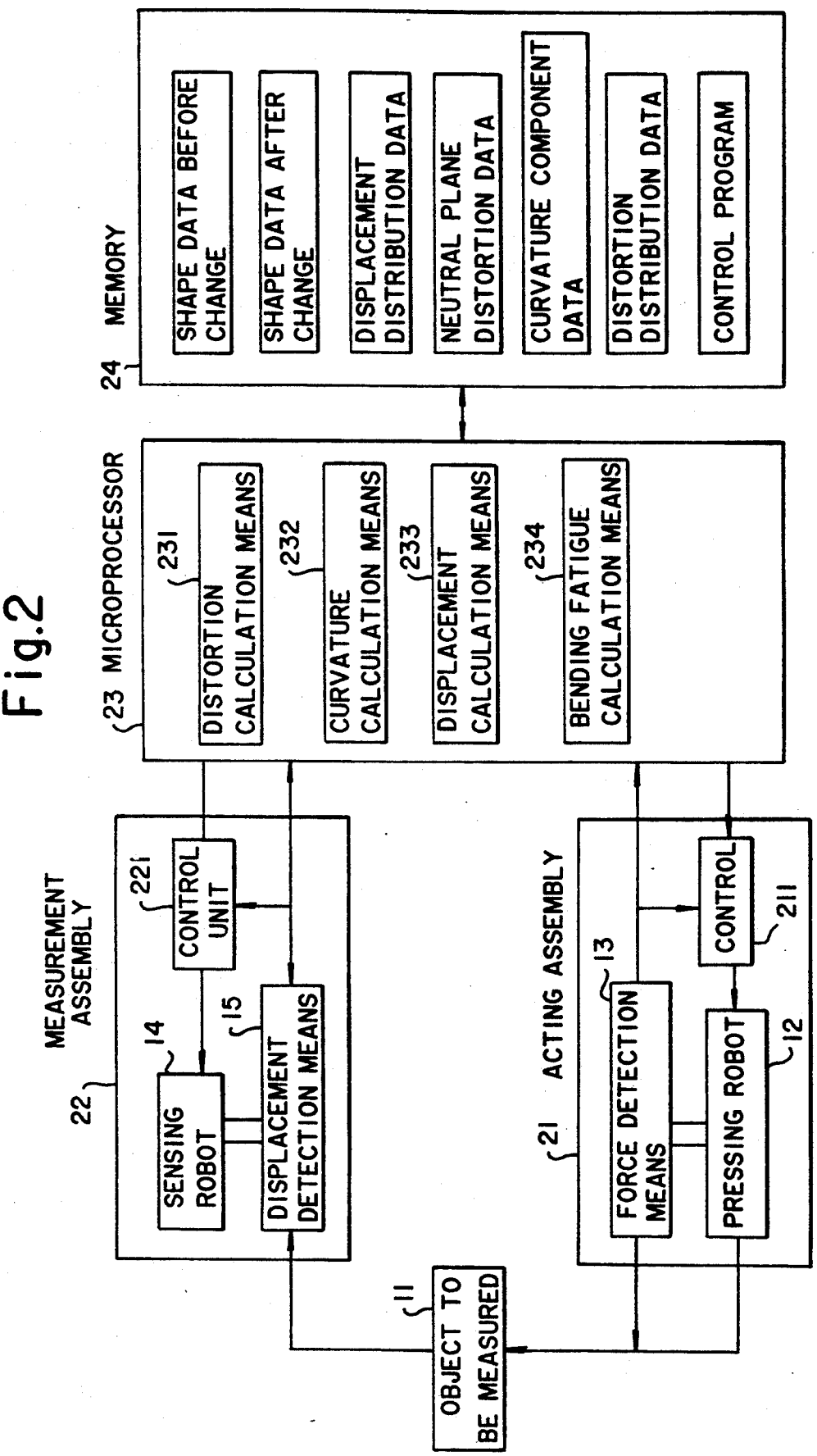
FIG. 2 is a basic block diagram of the robot measuring system according to the present invention.

FIG. 2 is a basic block diagram of the robot measuring system according to the present invention. In the drawing, the robot measuring system is composed of an acting unit adding a predetermined pressing force to the object 11, a measuring unit 22 for measuring the deformation in the object 11, a microprocessor 23 for calculating the displacement, distortion, curvature etc. based on the measured data, and a memory 24 for storing various data.

The acting unit 21 is composed of the pressing robot 12, a force detection means 13 acting as an inner force sensor, and a control unit 211 for controlling the pressing robot 12.

The measuring unit 22 is composed of the sensing robot 14, a displacement detection means 15 acting as a displacement gauge, and a control unit 221 for controlling the sensing robot 14.

The microprocessor 23 comprises various measurement means as explained below. That is, displacement measuring means, distortion measuring means, curvature measuring means, and bending fatigue measuring means etc.

The memory 24 stores shape data before and after the deformation, a displacement distribution function data, a neutral plane distortion data, a distortion distribution data, a curvature component data, a control program etc.

Figure 3:
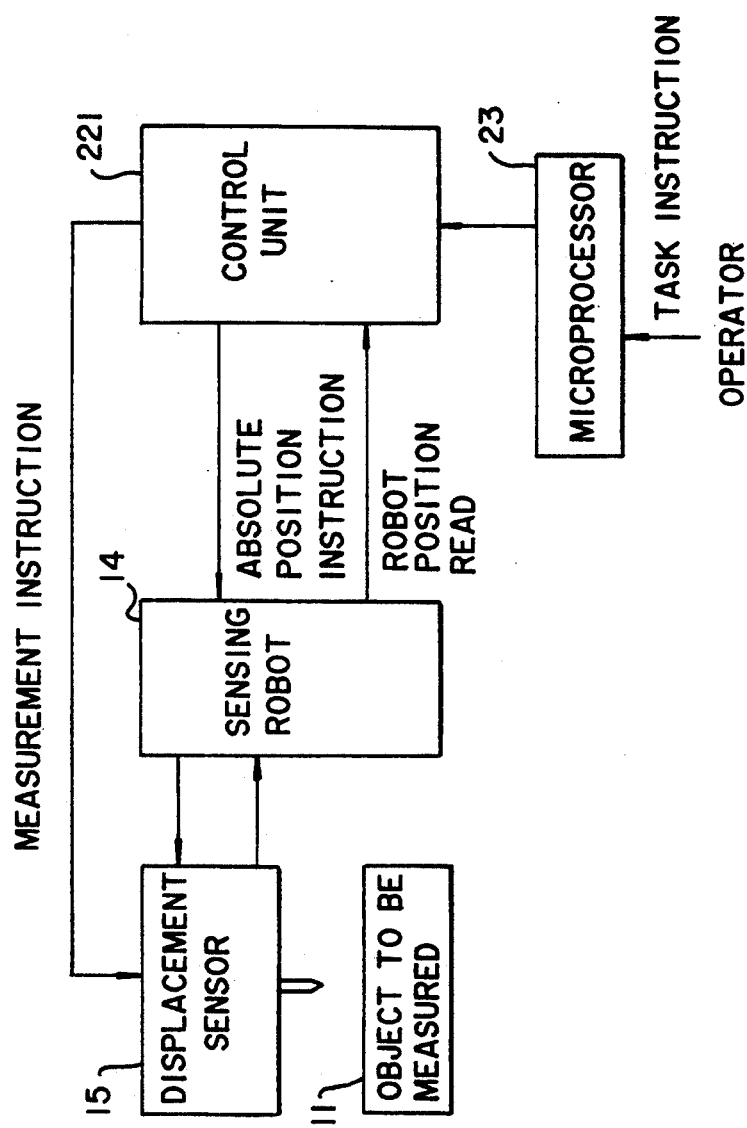
FIG. 3 is an illustration of a positioning control of a sensing robot in the robot measuring system according to the present invention.

FIG. 3 is an illustration for explaining a position control of the sensing robot 14 in the robot measuring system 10 according to the present invention. In the robot measuring system 10, a predetermined pressing force (a load) is applied to every very small area of the object using the pressing robot 12, and the displacement of respective measuring points is sequentially measured. An operator uses two methods for instructing a task to the control unit to control the sensing robot 14. That is, ① the method wherein absolute positions of all measuring points are instructed to all robots (a robot absolute position movement instruction), and ② the method wherein a first measuring point is designated as an absolute position, after the first measuring point is designated, each unit motion (a unit step) is repeatedly and sequentially instructed to the robots (a robot relative position movement instruction).

The method ① requires many movement instructions to the sensing robot during operation, so that the operators are very busy and therefore the method ② is usually employed.

However, due to repeating of the relative movement instruction in the method ②, the measurement is deteriorated because of accumulating of errors caused by calculation, an encoder, vibration etc.

An acting control of the sensing robot 14 according to the invention allows the control unit 221 to store a reference point used for the relative movement and to give a reference name thereto and also to give the identified names to each unit step of the relative movement. In the movement of the sensing robot 14, a target position is expressed by the sum of the reference position and the product of a unit step quantity and a step coefficient, as follows;

(target position=(reference position)+(unit step quantity)×(step coefficient)

The sensing robot 14 is moved by calculation of the above equation.

As shown in FIG. 3, upon receiving the task instruction from the operator through the microprocessor 23, the control 221 interprets the task instruction, and generates the absolute position instruction to the sensing robot 14, and further generates a measurement instruction. Then, a read position of the sensing robot 14 is fed back to the control 221.

FIG. 4 is an example of the movement and measurement commands instructed by the operator in FIG. 3.

In FIG. 4, assume that the ten measuring points are aligned from the position (0, 0, 50) in the direction X at an interval of 10 mm on the object 11, and the operator gives the commands to the control unit 221 as a task instruction.

The first, the memory (not shown) within the control unit 221 registers both "SOKU 0 0 50" showing a start point (0, 0, 50) of measurement carried out by "SET" instructions ① and ②, and "STEP 10 0 0" showing a distance 10 between the measuring points.

The next, in a "MOVE" instruction ③, step coefficient=3, unit step quantity=STEP=(10, 0, 0), and reference position=SOKU=(0, 0, 50) are obtained, thus the sensing robot is moved to the calculated target position=(30, 0, 50).

In the same manner as above, a target position calculation and an absolute movement are performed in MOVE instructions ④ and ⑤. In the MOVE instruction 4, because the step coefficient is not designated, then the step coefficient=1, and the absolute movement to the target position=(10, 0, 50) is executed. In the MOVE instruction ⑤, because the unit step quantity is not designated, then the unit step quantity=(0, 0, 0), and the absolute movement to the target position=the reference position (SOKU)= (0, 0, 50) is carried out.

Instructions ⑥ through ⑨ form a loop at an actual measurement operation, and "LOOP 10" in the instruction 6 designates repeating ten times of the loop.

The MOVE instruction ⑦ designates "LOOP" as a step coefficient that is a loop counter value showing the number of times of passing the loop. The loop counter (not shown) is provided in the control unit 221 for determining the number of times of repeating the loop.

The loop counter is reset ar "0" on its starting, and is added by +1 in every turn of the loop. Therefore, the target position of the MOVE instruction ⑦ is carried out by an absolute movement sequentially along with the measuring points, firstly (0, 0, 50), next (10, 0, 50), then (20, 0, 50), - - - , and finally (90, 0, 50). The measurement is performed in every time of movement by the measurement instruction ⑧ for automatically routing a total of ten measuring points.

Figure 5:
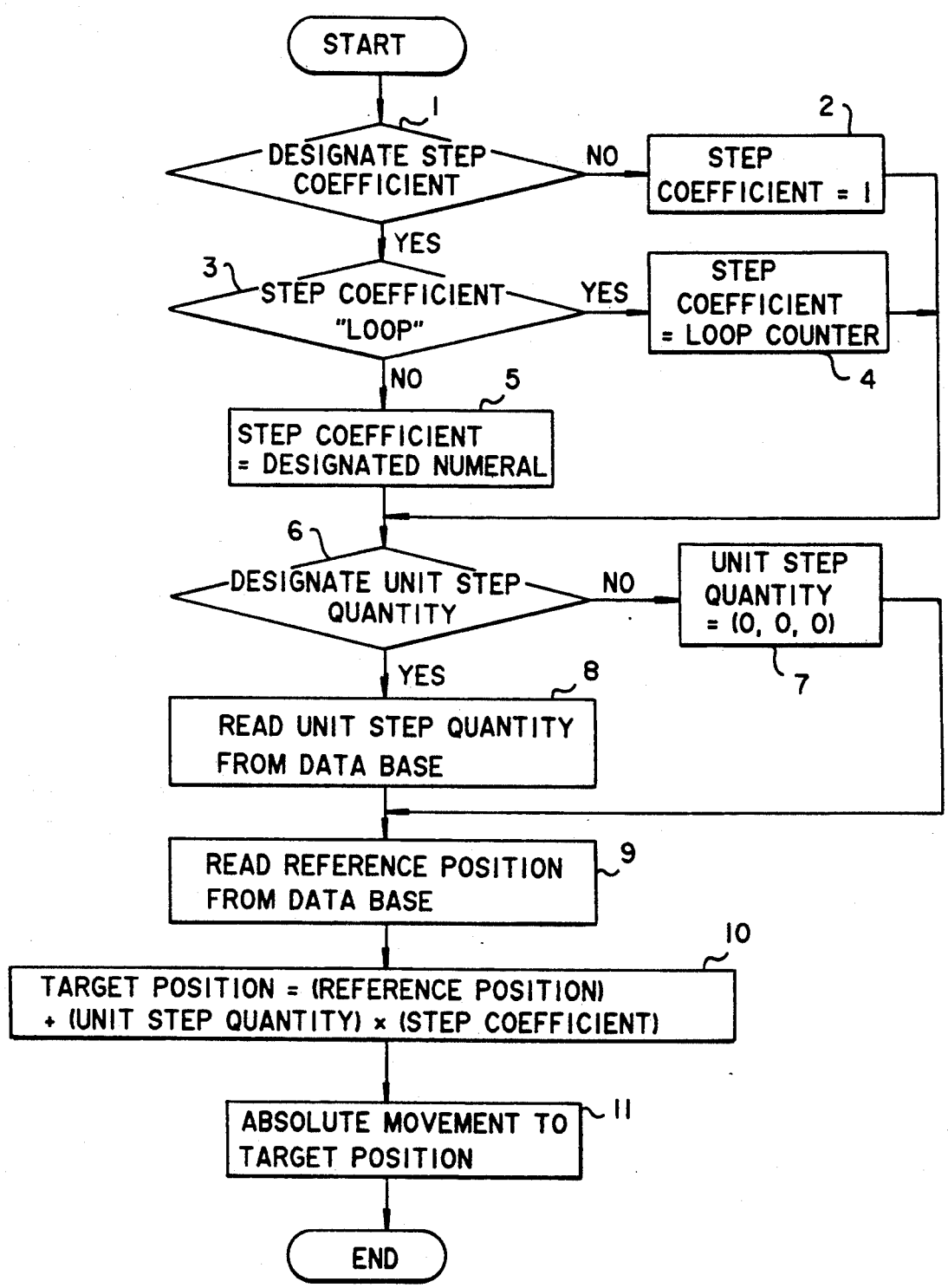
FIG. 5 is a flowchart of showing the process of the MOVE commands in FIG. 4.

FIG. 5 is a flowchart of the MOVE instruction shown in FIG. 4. In the step 1, the decision is made as to whether or not the step coefficient is designated, and when the step coefficient is not designated, then in the step 2, "step=1" is designated, and when the step coefficient is designated, in the step 3, then the decision is made as to whether or not the step coefficient is "LOOP".

When the step coefficient is "LOOP", the step coefficient becomes the loop counter value in the step 4, and when not "LOOP", it becomes the designated numerical value in the step 5.

The decision is made as to whether or not the unit step quantity is designated in the step 6, and when the unit step quantity is not designated, then unit step quantity=(0, 0, 0) is formed, and when it is designated, then in the step 8 the unit step quantity is read from a data base within the memory.

The reference position is read from the data base in the step 9, the calculation is performed in the step 10 as;

(target position=(reference position)+(unit step quantity)×(step coefficient), and an absolute movement is carried out to the target position in the step 11.

Figure 6:
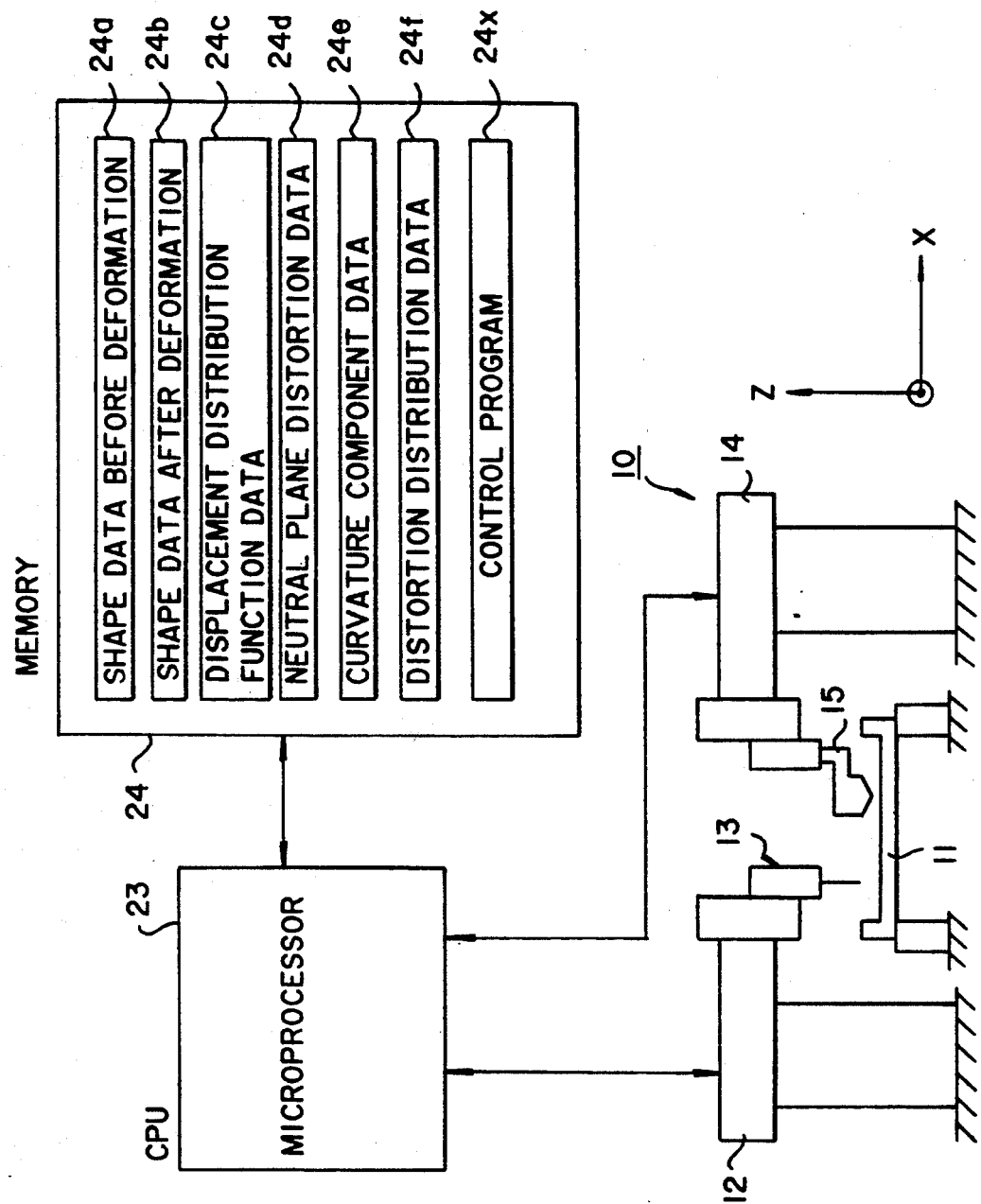
FIG. 6 is a block diagram of a distortion measurement device according to the present invention.

FIG. 6 is a block diagram of a measuring device for measuring distortion according to the present invention. Reference numeral 10 depicts a rectangular robot shown in FIG. 1, which comprises the acting unit and the measurement unit shown in FIG. 2. Reference numeral 23 corresponds to the microprocessor and 24 to the memory, in FIG. 2. In the memory 24 are provided regions 24a to 24f for storing the measured data and the calculated data and a region 24x for storing the control program. The former is composed of shape data before the occurrence of deformation, shape data after the occurrence of the deformations, displacement distribution data, distortion data at a neutral plane, curvature component data, distortion distribution data etc. These measured and calculated data are written to or read from the microprocessor (CPU) 23. The CPU 23 reads the control program 24x to instruct the robots.

The explanation is given to the distortion of the test piece below.

FIG. 7A shows the condition before the deformation is occurred in the test piece of a flat plate, i.e., before the measurement is performed. FIG. 7B shows the condition after the flat plate has been deformed by a pressing force P. The coordinates have axes X-Y-Z, and for convenience of explanation, refer to the example in occurrence of the deformation in the direction X as follows.

In FIG. 7B, it is known that, in a small displacement, distortion hardly arises substantially at the center portion in the thickness direction of the flat plate 11. Such plane having distortion "0" is called as a "neutral plane". The present invention adopts the word "neutral plane" as an imaginary plane meaning that the bending distortion is considered "0". The flat plate has the neutral plane substantially at the center plane of the thickness thereof. Accordingly, the given point having a distance "z" from the center plane becomes about ½ of the thickness at the surface thereof.

Then, the distortion $\epsilon_{xx}$ in the axis direction X with a distance z from the center plane is proportional to an inverse number of the curvature radius and expressed by the following equation;

$$\epsilon_{xx} = z/r_{xx}$$

where $r_{xx}$ represents a curvature radius of the curve along with the axis X on the flat plate.

In the same manner, the distortion $\epsilon_{YY}$ in the axis direction Y with the distance z from the center plane is expressed by the following equation;

$$\epsilon_{YY} = z/r_{YY}$$

where $r_{YY}$ represents a curvature radius of the curve along with the axis Y on the flat plate as the drawing.

The shearing strain $\epsilon_{XY}$ is expressed by the following equation;

$$\epsilon_{XY} = z/r_{XY}$$

where, in connection with the above, hereinafter for the distortions, refer to as $\epsilon_{XX}$, $\epsilon_{YY}$, $\epsilon_{XY}$, and for the curvature radii, refer to as $r_{XX}$, $r_{YY}$, $r_{XY}$.

Here, $1/r_{XX}$ that is the inverse of the curvature radius $r_{XX}$ represents the curvature. The curvature can be obtained by processing the partial differential of second order of a displacement distribution "w" of the flat plate relative to "x". The partial differential equation of second order is as follows;

$$\frac{1}{r_{XX}} = -\frac{\partial^2 w}{\partial x^2}$$

$$\frac{1}{r_{YY}} = -\frac{\partial^2 w}{\partial y^2}$$

$$\frac{1}{r_{XY}} = -\frac{\partial^2 w}{\partial x \partial y}$$

Therefore, the distortion distribution is obtained from the differential value of the displacement curvature or its approximate value which is attainable from discrete data of the displacement measured. Since a material characteristic is considered as linear for the slight distortion, a stress distribution is obtained from the distortion distribution.

Figure 8:
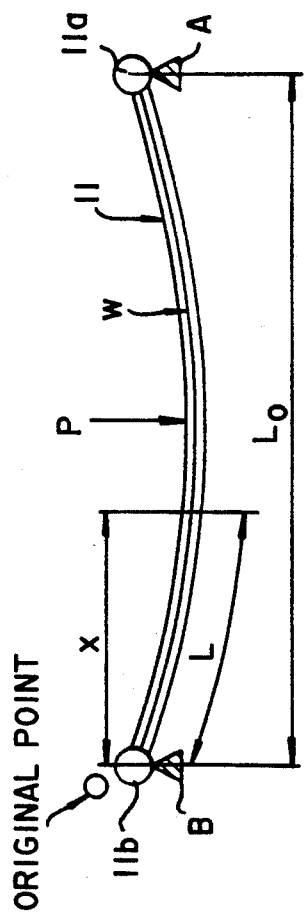
FIG. 8 is an illustration for explaining the distortion distribution of an object.

FIG. 8 is an illustration of the distortion in the flat plate whose edge is reinforced by ribs. The plastic molded article with thin thickness is very often provided on the edge of the plate with the reinforcing ribs as shown in the drawing. With a large pressing force added to such thin plate, a great deformation occurs in the plate and an extension of the neutral plane thereof becomes appreciable. As a result, the distortion of the neutral plane takes place as an important factor.

As shown in FIG. 8, the flat plate 11 is supported at supporting points A and B through ribs 11a and 11b on its both ends. This construction corresponds to bending of a beam supported at its both ends. If a force P is added above the flat plate 11, the plate 11 is distorted as shown in the drawing. Symbol $L_0$ expresses a projected length on the axis X as to the plate 11 distorted, and the projected length is constant (that is, beam length). Assuming the bent curve "w" of the neutral plane caused by the force P on the plate 11, a length L along with the plate 11 distorted and with a distance "x" apart from an origin "O", is represented by the following equation;

$$L = \int_0^K \left\{ 1 + \left(\frac{\partial w}{\partial x}\right)^2 \right\}^{\frac{1}{2}} dx \quad (1)$$

where, assuming $dw/dx \ll 1$, then the above equation becomes as follows;

$$L = \int_0^K \left\{ 1 + \frac{1}{2}\left(\frac{\partial w}{\partial x}\right)^2 \right\} dx \quad (2)$$

The extension $U_x$ of the neutral plane at the position with the distance "x" apart from the origin "O", satisfies the following equation;

$$U_x = \int_0^K \frac{1}{2}\left(\frac{\partial w}{\partial x}\right)^2 \quad (3)$$

Accordingly, the distortion occurs in the neutral plane because of the relatively large bending. This distortion $\epsilon_0$ is represented by the next equation;

$$\epsilon_0 = \frac{1}{2}\left(\frac{\partial w}{\partial x}\right)^2 \quad (4)$$

Due to the equation above, the distortion caused on the flat plate 11 receiving the bending force, is equal to a sum of the distortion obtained from the curvature and the distortion produced by the extension of the neutral plane. Such distortion $\epsilon_x$ in the axis direction X (vertical distortion) is expressed by the following equation;

$$\epsilon_x = -z\left(\frac{\partial^2 w}{\partial x^2}\right) + \frac{1}{2}\left(\frac{\partial w}{\partial x}\right)^2 \quad (5)$$

In the same manner, the distortion $\epsilon_y$ in the axis direction Y (vertical distortion) is expressed by the following equation;

$$\epsilon_y = -z\left(\frac{\partial^2 w}{\partial y^2}\right) + \frac{1}{2}\left(\frac{\partial w}{\partial y}\right)^2 \quad (6)$$

In the same manner, the distortion $\epsilon_{xy}$ in the axis direction XY (shearing strain) is expressed by the following equation;

$$\epsilon_{xy} = -z\left(\frac{\partial^2 w}{\partial x \partial y}\right) + \frac{1}{2}\left(\frac{\partial w}{\partial x}\right)\left(\frac{\partial w}{\partial y}\right) \quad (7)$$

Figure 9:
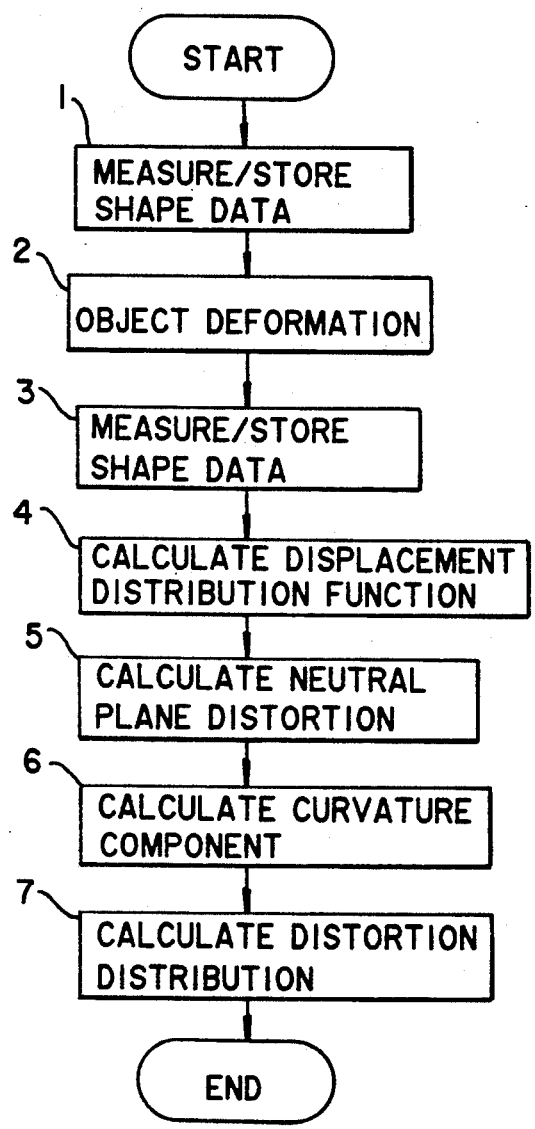
FIG. 9 is a flowchart showing the operation of the device in FIG. 6.

FIG. 9 is a flowchart for explaining the operation of the measuring device in FIG. 6.

In the step 1, the CPU 23 allows the sensing robot to move depending on the control program 24x within the memory 24, and measures the positioning coordinates in the axis direction Z in every predetermined measuring point in the plane X-Y on the object 11. The data of the positioning coordinates thus obtained, is stored in a shape data storing region 24a before occurrence of the deformation in the memory 24 by means of the CPU 23.

In the step 2, the CPU 23 allows the pressing robot 12 to act, and forces the pressing rod at the head of the inner force sensor 13 against the object. To obtain a predetermined pressing force P, the CPU 23 controls the pressing force of the robot 12 depending on the output of the inner force sensor 13.

In the step 3, the coordinates position in the axis direction Z on the object 11 in the condition of deformation by bending, is measured by the displacement gauge 15 on the same measuring position as above-mentioned. Resultant data thus measured are stored in the shape data storing region 24b after occurrence of the deformation.

In the step 4, after measuring the shape data in the timing before and after the occurrence of the deformations, the CPU 23 calculates the displacement distribution "w" in accordance with the shape data.

The calculation of the displacement distribution "w" can be obtained using the spline smoothing method of order 3 explained later according to the present invention.

By obtaining the displacement distribution "w" using the spline smoothing method, the displacement data at the optional position can be obtained. However this optional position excludes the measuring points designated from the discrete type shape data which are measured before and after the occurrence of the deformation and stored in the memory regions 24a and 24b. Further, it becomes possible to process a mathematical expression, for example, the differential.

The displacement distribution "w" thus obtained is stored in the storing region 24c as a displacement data.

In the step 5, the CPU 23 firstly calculates the distortion of the neutral plane appearing on the second term in the right side of the respective equations (5) to (7), based on the displacement distribution "w". The calculated data is stored in the region 24d.

In the step 6, the CPU 23 calculates the curvature component of the first term in the right side of the respective equations (5) to (7).

As is obvious from the equation, the first term in the right side thereof is obtained in such a way that the partial differential value of second order with respect to the displacement distribution "w" is multiplied by the distance "z" in the thickness direction of the object to be measured.

The resultant data thus calculated, is stored in the storing region 24e of the memory 24 as a curvature component data.

In the step 7, the CPU 23 reads the distortion data of the neutral plane and the curvature component data, and calculates a sum of those two data in accordance with the equations (5) to (7). Then, the CPU 23 can obtain the distortion distribution.

However, the present invention is not limited to the description using the flat plate, i.e., the object 11, provided on its edge with the reinforced ribs. For example, in the object 11 with the grid type ribs, the measurement of the distortion distribution is performed by determining the displacement distribution in every unit region so as to avoid the influence of the ribs.

In this way, the measurement of the distortion is carried out firstly for the shape data in the timing before and after the deformation occurrence in the object 11, and the displacement distribution "w" is obtained from the difference of shape data before and after the deformation occurrence using the spline smoothing method of order 3. The next, the distortion of the neutral plane of the object is calculated from the equations as to the distortions described above, and the curvature component is also attained therefrom. The distortion distribution can thus be obtained from the sum of the neutral plane distortion and the curvature component.

If the distortion of the neutral plane is negligibly small, the distortion distribution is derived from only the curvature component data.

For the detailed explanation as to the calculation of the displacement distribution "w", refer to as follows. As is obvious from the first term in the right side of the respective equations (5) to (7), the partial differential of second order must be "x" in the displacement distribution "w". The partial differential of second order is obtained by passing the eight measuring points using a polynomial of order $n-1$, where "n" is the number of the measuring points. However, it requires a very complicated function to express the displacement distribution "w" passing through the eight measuring points using a function for all the definition region (the domain). In general, since the polynomial having higher order "n" tends to introduce vibration of solution at a differential value, it is not suitable for the calculation including many measuring points as above. Conventionally, the spline interpolation formula has been introduced for solving such problem.

The spline interpolation method divides all the regions (the domains) to be processed into some finite sections, at which the polynomials formula of order "m" lower than "n" are allotted. The polynomials with the lower order can thus be easily expressed. If the polynomials in all the sectional regions are formed as continuous at the respective contact points (that is, boundaries between any two of the divided sections), then the continuous function with the lower order can easily be obtained. Of such functions expressed by the polynomials of order "m", the function with a continuous and having a differential value of $(m-1)$-th order over all the domain, is a spline function of order "m".

Therefore, the spline function having the order not less than 3 ($m=3$) satisfies the condition (the differential of second order is possible, the curvature physically obtained is continuous) of the approximate expression approximating the displacement distribution.

However, because the spline interpolation formula defines the displacement function to certainly pass through the measuring points, the calculation accuracy is deteriorated due to a measurement error on the differential processing. Accordingly, in the presence of the relatively smaller measuring error in comparison with the displacement quantity, the curvature radius can be measured at a certain degree of accuracy even in using the spline interpolation formula. However, in the relatively smaller displacement quantity, influence of the measuring error becomes larger, and it is difficult to calculate the accurate curvature using the spline interpolation formula.

The present invention, therefore, adopts the spline smoothing method to obtain the displacement function "w". The spline smoothing method can obtain a displacement more approximating a real value, without passing through the measuring points. That is, the spline smoothing method employs a smoothing method similar to the least-square approximation on calculating of the spline function.

Figure 10:
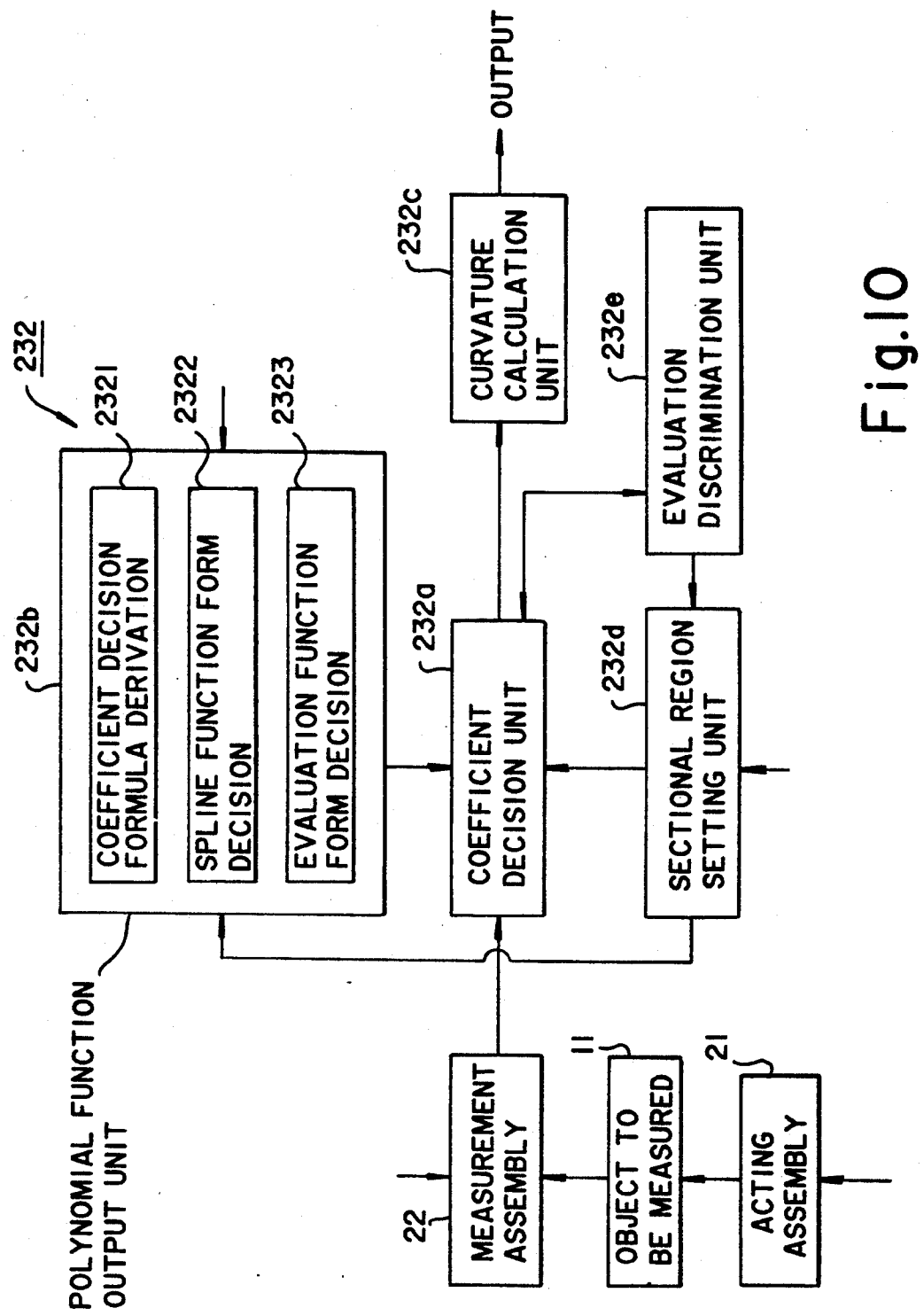
FIG. 10 is a basic block diagram of a curvature calculation device using a spline smoothing method according to the present invention.

FIG. 10 is a basic construction view of the curvature calculation device using the spline smoothing method according to the present invention.

As described above, the curvature in the axis direction X is an inverse number $1/r_{XX}$ of a curvature radius $r_{XX}$, and further its inverse number is obtained by processing the partial differential of second order using a distance "x" for the displacement distribution "w" of the flat plate. The curvature in the axis direction Y is obtained in the same way. A shearing factor is obtained by performing the partial differential of second order using x and y for the displacement curvature. In general, "curvature" is defined as a limit of $\Delta s \to 0$ wherein an angle forming a tangent at point P with a tangent at point P' is $\Delta \omega$ when point P moves along with curve $\Gamma$ by a length $\Delta s$ of an arc to reach point P'.

Referring to FIG. 10, reference numeral 232 is the curvature calculation means contained in the microprocessor 23 as shown in FIG. 2. The curvature calculation means 232 is composed of a sectional region setting unit 232d for dividing the measuring region of the object 11 into a plurality of regions based on the predetermined evaluation quantity, a polynomial/function output unit 232b for outputting both the sectional polynomials including an indeterminate coefficient expressing the displacement quantity of the object 11 in every region and the evaluation function evaluating the extent of approximation obtained by that sectional polynomials, a coefficient decision unit 232a for determining the indeterminate coefficient of the polynomial at least based on the evaluation function, the displacement quantity measured, and a boundary condition between the regions, and an evaluation quantity decision unit 232e for instructing the re-dividing of the measuring regions to the sectional region setting unit 232d if the sectional regions divided from the region are decided unsuitable after such decision is made on the basis of the evaluation quantity derived from the evaluation function.

The polynomial/function output unit 232b comprises a coefficient decision formula derivation 2321, a spline function form decision 2322, and an evaluation function form decision 2323, which are explained below.

The acting assembly 21 adds the predetermined displacement to the object 11, and the measurement assembly 22 measures the displacement quantity in the measuring points with the number of n+1.

As described above, the polynomial/function output unit 232b outputs the sectional polynomial including the indeterminate coefficient for approximately expressing the displacement of the object 11 in every sectional region divided by the sectional region setting unit 232d.

In the above, if a maximum order of the sectional polynomial is, for example, order "m", then continuous differentials of m−1 times are obtained at the boundaries of the respective regions. The spline function ("m" is an odd number), for example, is used as a sectional polynomial in every region (t; t=1, 2, - - -, k) as follows;

$$f(x) = a_{t,m} x^m + a_{t,m-1} x^{m-1} + \ldots a_{t,1} x + a_{t,0} \quad (8)$$

where the indeterminate coefficients $a_{t,m}, a_{t,m-1}, \text{- - -}, a_{t,0}$ are determined by the condition explained later.

The "region" is defined as a region which is set on the object to be measured, and means the regions having 1, 2, and 3 dimension(s) respectively. For convenience of the explanation, assume regions (sections) with the number "k" obtained by dividing one dimension line segment [a, b]. The sectional regions in this case are expressed as the following equation;

$$[x_0, x_1], [x_1, x_2], \ldots \ldots, [x_{k-1}, x_k] \quad (9)$$
$$a = x_0, b = x_k$$

Nodal points $x_0, x_1, \text{- - -}, x_k$ of the boundaries produced by each sectional region in this invention are irrespective of the n+1 measuring points measured by the measurement assembly 22 as different from the conventional spline interpolation formula. The position of the nodal point is determined not depending on the position of the measuring point but based on designation from the external or the evaluation quantity. Therefore, the number n+1 of the measuring points are not identical with the nodal number "k".

On the other hand, the evaluation function is used for evaluating the extent of approximation obtained using the sectional polynomial. Since the conventional spline interpolation formula passes through the measuring points without failure, the evaluation function is unnecessary. However, in the present invention, because the restriction is not imposed on passing through the measuring points, the evaluation function must be required.

More specifically, in this invention the displacement expressed by the sectional polynomial at the measuring points and the measured displacement are not required to completely coincide each other, and the evaluation function capable of evaluating the degree of approximation of the polynomial is introduced so that the polynomial more approximates the real displacement.

The example of such evaluation function are shown wherein square of difference between the displacement quantity expressed by the polynomial and the measured displacement quantity is summed from all the measuring points, or wherein an absolute value of the difference between the same is summed from all the measuring points, or further as shown in following equation;

$$\sigma = \sum_{i=1}^{n} W_i |(s(x_i) - y_i)|^2 + g \int_b^a (f^{(m)}(x))^2 dx \quad (10)$$

where $w_i$ and g represent a weight function, $s(x_i)$ is a spline function, $y_i$ is a measured data, "m" is a spline function, and "i" represents a parameter showing a position of the measuring point.

The evaluation function of the above equation (10) means the description undermentioned. In smaller value of "g", the first term is mainly evaluated and the truth of the measured data is a prime object. In larger value of "g", the second term is mainly evaluated and the smoothness is a prime object. The present invention places the prime object on the truth for the measured value and permits the respective measured data to carry the same weight. For this object, the following equation is used as an evaluation function in the invention;

$$\sigma = \sum_i W_i |(s(x_i) - y_i)|^2$$

where $W_i = 1$ (i=1 to n), and g=0.

The coefficients of the sectional polynomials which are set by the polynomial/function setting unit 232b, are determined by the evaluation function, and the displacement quantity measured by measurement assembly 22, and the possible condition for the continuous differentials of m−1 times which the sectional polynomials must satisfy at the boundaries of regions subjected to setting by means of the sectional region setting unit 232d.

In the above process, the evaluation discrimination unit 232e determines whether or not the sectional region subjected to the setting is suitable in accordance with the evaluation value (output from the evaluation function) determined based on the sectional region formed by the setting unit 232d.

More specifically, as in the former explanation, assume the evaluation function wherein square of difference between the displacement quantity expressed by the polynomial and the measured displacement quantity is summed from all the measuring points. Then, in the absence of the measuring error, the approximation is upgraded with the decrease of the evaluation value. However in the presence of the measuring error, even with the evaluation value lowered under a certain level, the approximation is not always improved. This is apparent from the fact that the evaluation value does not become zero even in using a truth function in the presence of the measuring error.

Accordingly, in the presence of the measuring error, the predetermined threshold estimated from the error of a measuring system is firstly set, and a decision is made as to whether or not the divided region is suitable, depending on the evaluation value more or less than the threshold value, respectively. If the evaluation value is larger, an instruction is input to the sectional region setting unit 232d to execute a further dividing process.

Figure 11:
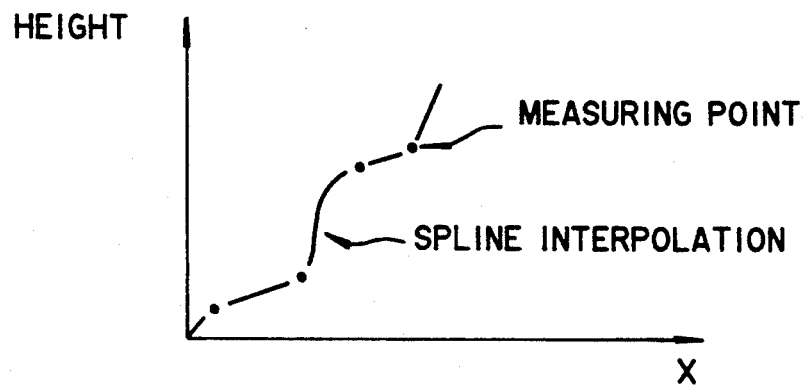
FIG. 11 is an illustration for explaining the conventional spline interpolation formula.

FIG. 11 is an illustration for explaining the conventional spline interpolation formula. As shown in the drawing, the spline interpolation formula realizes the path through the each measuring point without failure. From this reason, the measuring data surely includes errors, and with relatively smaller displacement quantity, it is difficult to calculate the curvature with a high accuracy because of suffering larger deterioration due to the measuring error.

Figure 12:
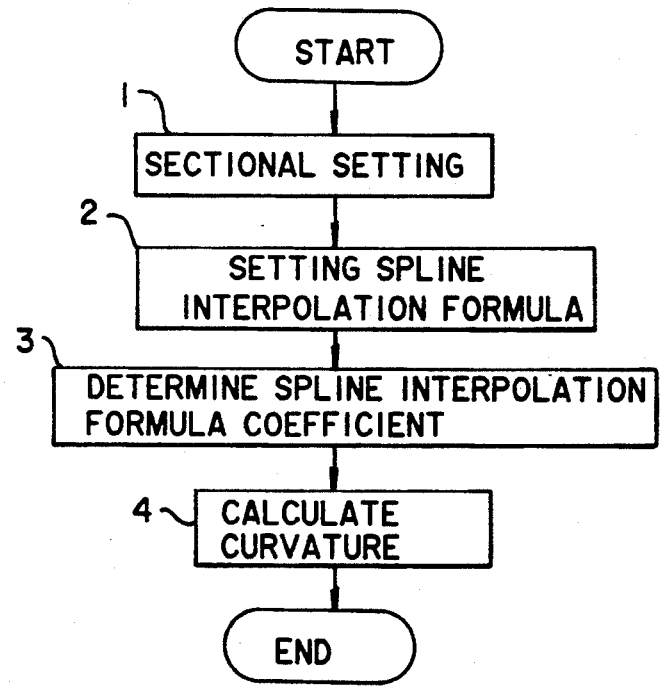
FIG. 12 is a flowchart for explaining the conventional curvature calculation.

FIG. 12 is the conventional processing flowchart of the curvature calculation. Conventionally, in the step 1, a region (section) having a plurality of measuring points as a nodal point, is set in advance, and in the step 2, the spline interpolation formula with the predetermined number of order (the lower number than the measuring points, for example, m=order 3) is set in every region so that the differentials of (m−1) times are continuously available. In the step 3, the respective coefficients are determined using the fact that the spline interpolation formula surely passes through the measuring points (the nodal points) and a derived function of the spline interpolation formula is continuous at the nodal points. In the step 4, the partial differential of second order is performed at the curvature calculation unit based on the spline interpolation formula thus obtained. The problems of the conventional system shown in FIGS. 11 and 12 have been explained and then the description thereof is omitted here.

Figure 13:
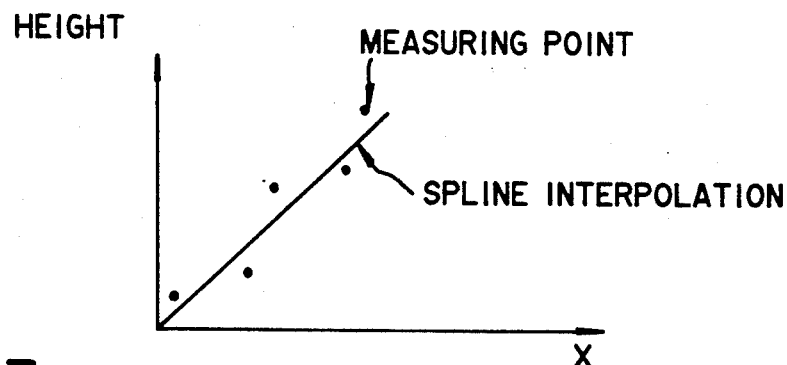
FIG. 13 is an illustration for explaining the spline smoothing method according to the present invention.

FIG. 13 is an illustration for explaining the spline smoothing method according to the present invention. As is obvious from the comparison with FIG. 11 showing the conventional spline interpolation formula, the spline smoothing method can greatly reduce the fluctuation caused by the measuring error.

Figure 14:
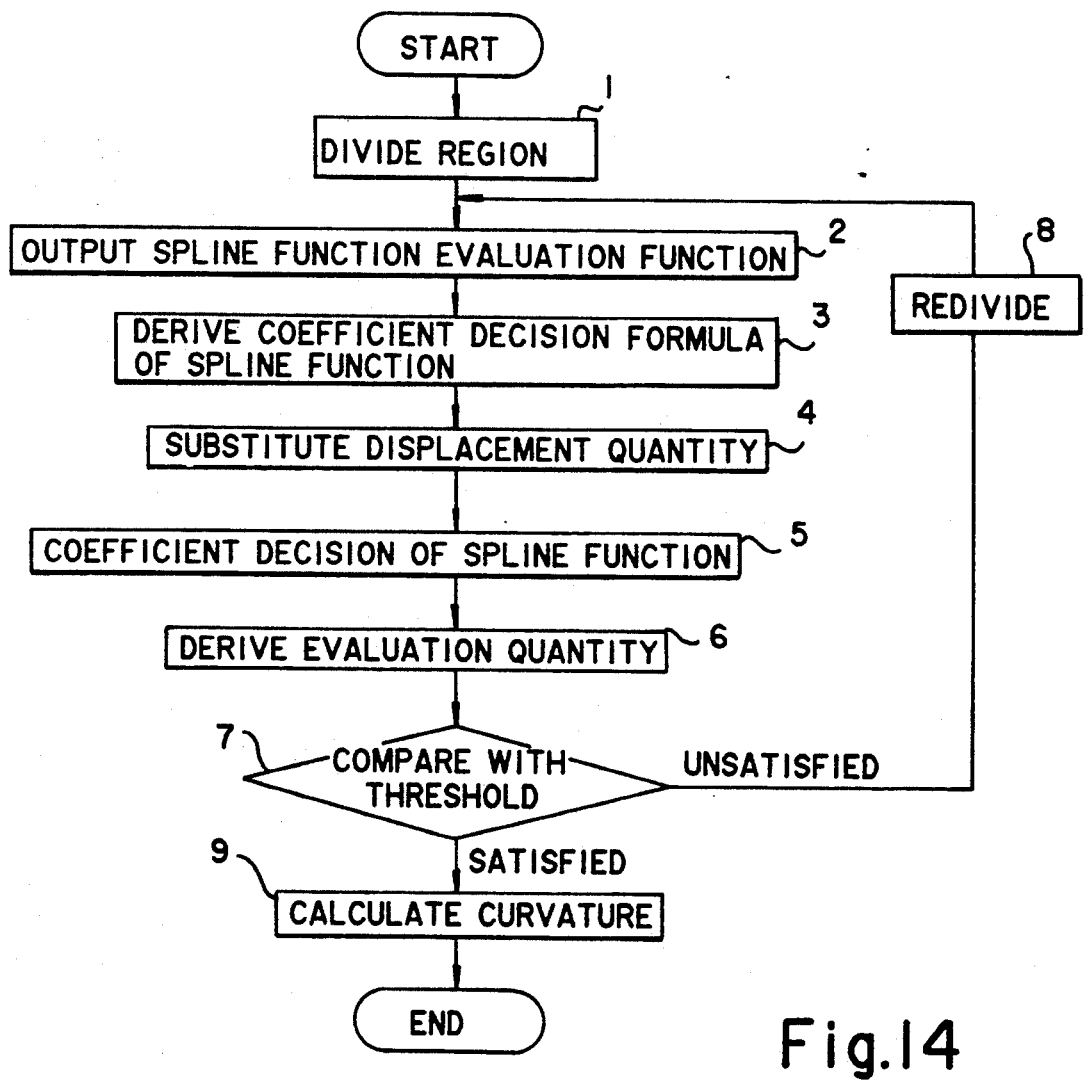
FIG. 14 is a flowchart for explaining the curvature calculation according to the invention.

FIG. 14 is a processing flowchart of the curvature calculation according to the invention. As shown in FIG. 10, the polynomial/function output unit 232b comprises in detail the coefficient decision formula derivation 2321, the spline function form decision 2322, and the evaluation function form decision 2323.

In the step 1, the number "k" of the sectional region and the measuring region [a, b] are set in advance by the sectional region setting unit 232d. For example, if the number of the measuring points is "n", "k" is set different from "n" to output (if k=n, then it becomes the same as the conventional spline interpolation formula).

In the step 2, the spline function form decision 2322, receiving the number "k" of the sectional region from the former step 1, allows the respective sectional regions to correspond to the polynomials of order "m" (an odd number, for example, 3) including an indeterminate coefficients. The evaluation function form decision 2323 determines the form of the evaluation function as above. As shown in FIG. 11, the equation is as follows;

$$\sigma = \sum_i W_i |(s(x_i) - y_i)|^2$$

where $W_i$ represents a weight function, $s(x_i)$ is a spline function, $y_i$ is a measured data, "i" is a parameter showing the measuring positions.

In the step 3, the coefficient decision form derivation 2321 derives a decision formula satisfied by the indeterminate coefficients of polynomials, from the spline function being set in every region and the evaluation function and the continuous condition to be established between the respective sectional regions.

The polynomials of order m (=3) corresponding to the sectional regions each with the number "k" are as follows;

$$s_j(x) = a_{j,3}x^3 + a_{j,2}x^2 + a_{j,1}x^1 + a_{j,0}$$

the regions being set by the sectional region setting unit 232d is;

$$[x_0, x_1], [x_1, x_2], \cdots, [x_{k-1}, x_k],$$

the boundaries (the nodal points) of the above regions are as follows;

$$x_0 (=a), x_1, x_2, \cdots, x_{k-1}, x_k (=b)$$

in the above boundary, the derived function of the spline function is;

$$s^{(c)}(x) \ (c=1, 2, \cdots, m-1)$$

using the respective expressions in the above, i.e., due to the boundary condition that the spline function and its derived function in the boundaries (the nodal points) of the regions being set by the sectional region setting unit 232d must be continuous and the condition that the value of the evaluation function must be minimized, then a decision formula to be satisfied by the indeterminate coefficients is derived on the basis of a formula formed from a variational principle.

In the step 4, the displacement quantity measured at respective measuring points is substituted in the above decision formula for the displacement added by the above decision formula and the acting assembly 21.

In the step 5, the indeterminate coefficients of the spline function are determined.

In the step 6, the evaluation quantity discrimination unit 232e substitutes the coefficient obtained from the coefficient decision unit 232a into the evaluation function to calculate an evaluation quantity $\sigma$.

In the step 7, the evaluation quantity $\sigma$ thus calculated is compared with the predetermined threshold $\sigma_0$, and if $\sigma$ is larger than $\sigma_0$, a decision is made as to whether or not an unsuitable region exists due to the sectional region setting unit 232d.

In the step 8, on decision made as an unsuitable region at the setting unit 232d in the former step 7, the instruction for re-dividing the regions into more sections is delivered to the sectional region setting unit 232d, and the processing restarts from the step 2.

In the step 9, if the evaluation quantity $\sigma$ is smaller than the threshold $\sigma_0$, then considering the region obtained from the sectional region setting unit 232d as a suitable one, the section polynomial having the coefficient determined by the sectional region setting unit 232d is outputted to the curvature calculation unit 232c as a displacement expression of the object.

Figure 15:
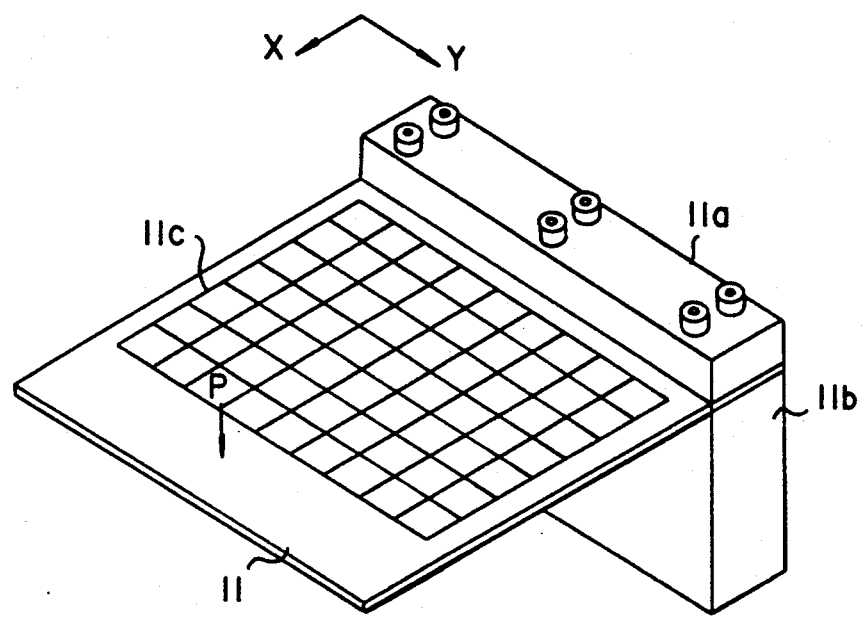
FIG. 15 is an illustration for explaining the holding state of the object to be measured.

FIG. 15 is an illustration of the mount of the object to be measured. As shown in FIG. 1, reference numeral 1 depicts the object 11, which is secured by proper securing means 11a and 11b. The object 11 is made of, for example, metal with a high linear property. Grid lines 11c shown on the surface thereof is illustrations for convenience of the explanation, and a displacement quantity is measured at each intersection of the grid lines 11c.

Figure 16:
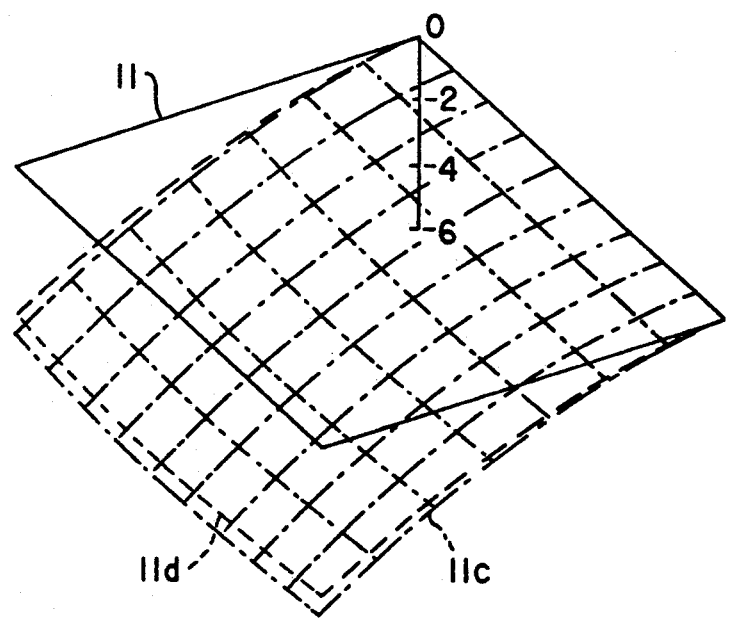
FIG. 16 is an illustration for explaining displacement quantity of the object to be measured.

FIG. 16 is an illustration of the displacement quantity of the object 11. Solid lines 11 show a reference plane of displacement "0" in the object. Chain dotted lines show the displacement in the timing after adding the pressing force. Chain dotted lines show the result of a structural analysis obtained by a finite element method for interest.

Figure 17:
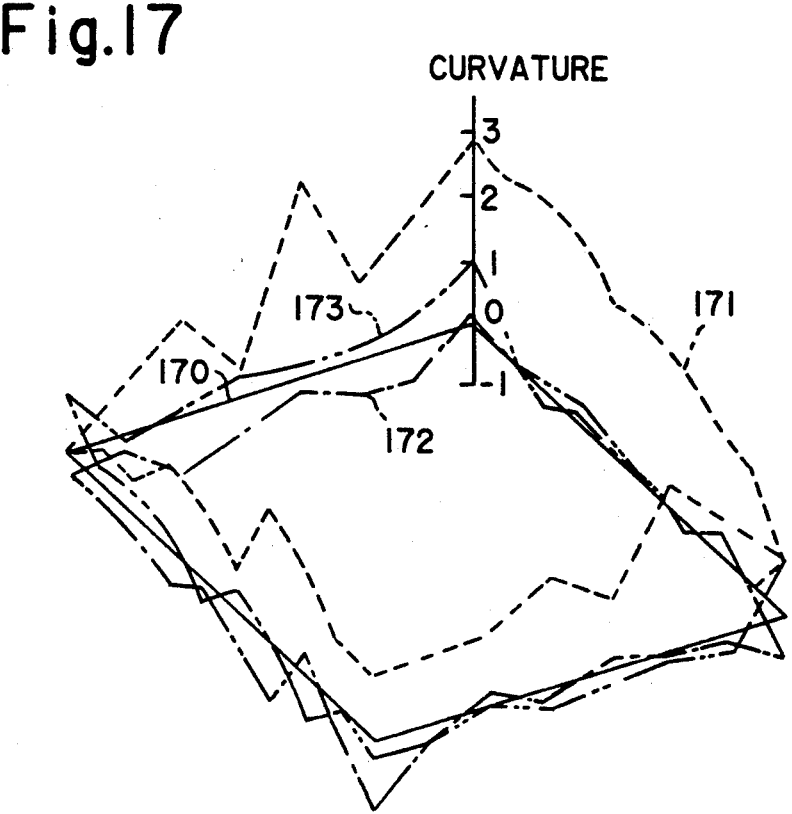
FIG. 17 is an illustration for explaining measured curvature data using a conventional method.

FIG. 17 is an illustration of the calculation result of the curvature obtained by the conventional method. Solid lines 170 show the reference plane of curvature "0". Dotted lines 171 show the curvature in the axis direction X, and lines 172 show the curvature in the axis direction Y. Two point chain lines 173 show a torsion. Apparently, the drawing shows difference in the actual curvature and torsion, and this indicates a disadvantage caused by the limitation to the stress measuring range.

Figure 18:
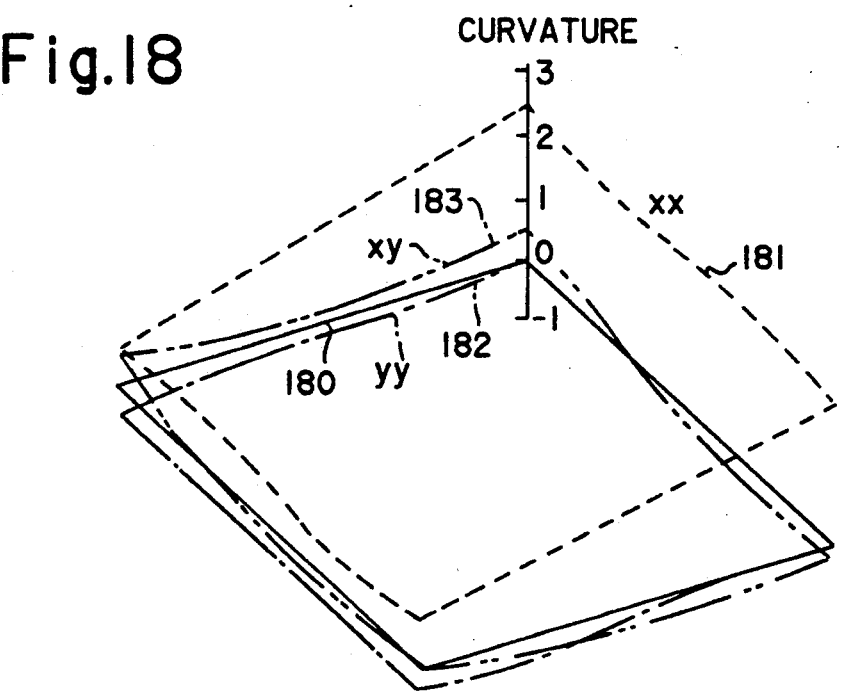
FIG. 18 is an illustration for explaining measured data of a curvature calculation using a calculation method according to the present invention.

FIG. 18 is an illustration of the calculation result of the curvature obtained by method according to the present invention. Solid lines 180 show the reference plane of the curvature "0". Dotted lines 181 show the curvature in the axis direction X, and one point chain lines 182 show the curvature in the axis direction Y. Two point chain lines 183 show the torsion. As is obvious from in comparison with FIG. 17, extremely high accurate curvature and torsion can be obtained.

Figure 19:
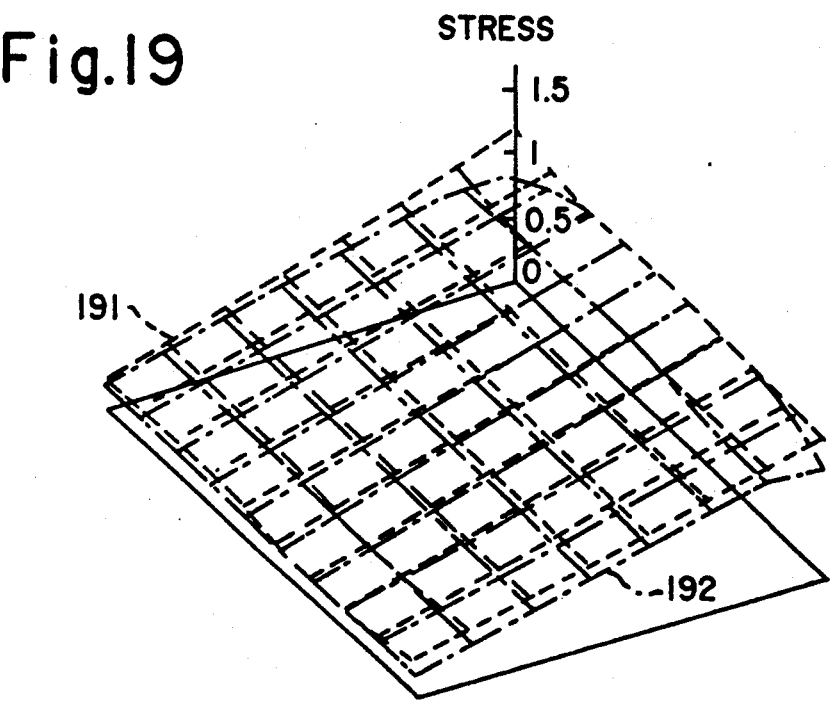
FIG. 19 is an illustration for explaining curvature comparison date and the finite element method.

FIG. 19 is an illustration in that a curvature 191 in the axis direction X obtained from FIG. 18 shown by dotted lines is compared with the result of a structural analysis obtained by the finite element method as shown by chain dotted line. Apparent from the drawing, the result according to the present invention is substantially equal to a theoretical value using the finite element method. Difference between the measured value and the theoretical value at the both ends of the stationary part is attributed to the difference in securing of the ends.

Figure 20:
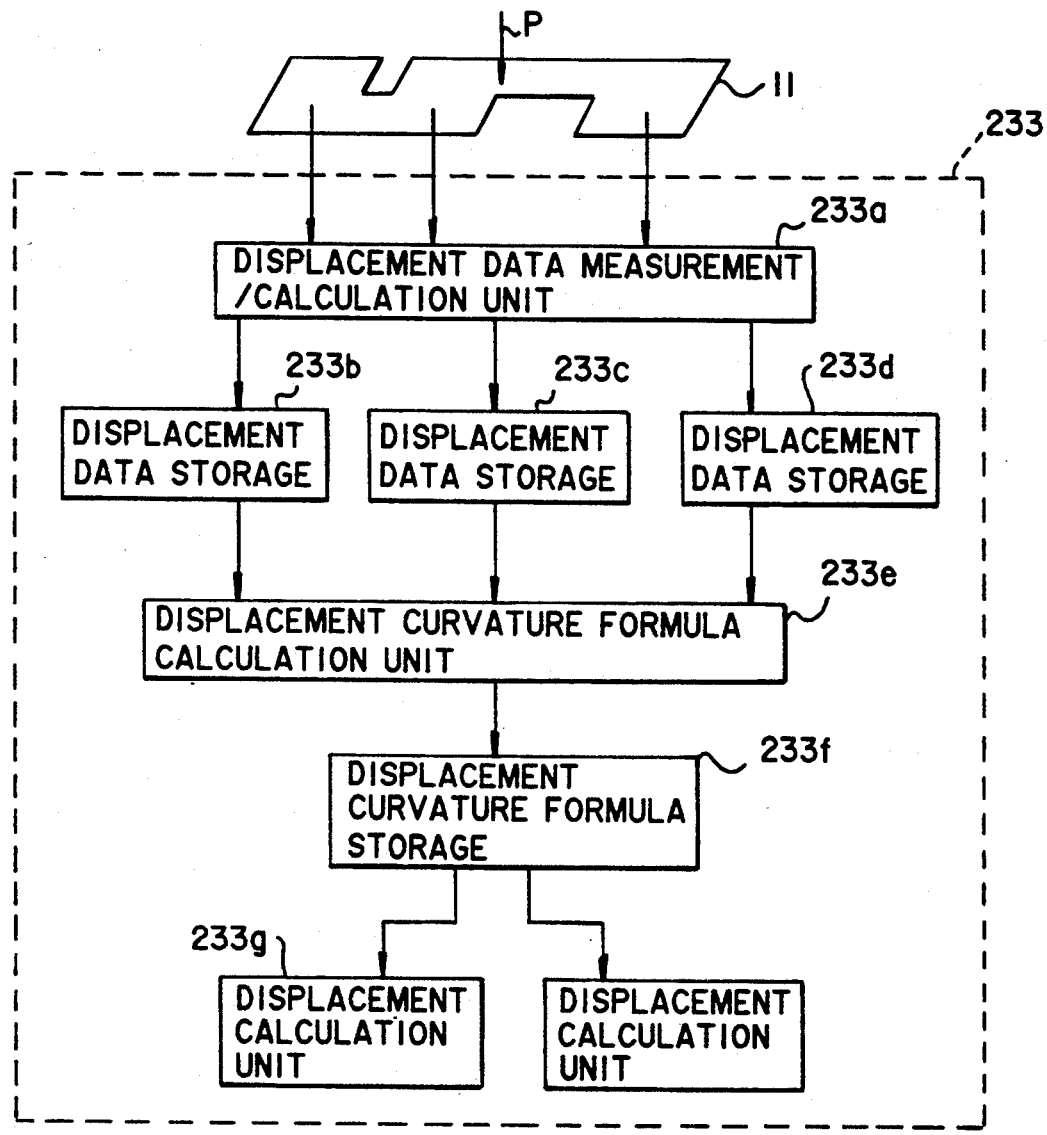
FIG. 20 is a block diagram of a displacement measurement/calculation unit according to an embodiment of the present invention.

FIG. 20 is a block diagram of an embodiment of a displacement measuring device according to the invention. The drawing shows an example of the object 11 partially having notches. Reference numeral 233 depicts a displacement calculation means within the microprocessor 23 in FIG. 2 and calculates the displacement with the pressing force P added to the object 11. The displacement calculation means 233 is composed of a displacement data measurement/calculation unit 233a, displacement data storages 233b to 233d, a displacement curvature formula calculation unit 233e, a displacement curvature formula storage 233f, and a displacement calculation unit 233g.

The displacement measurement/calculation unit 233a measures the shape data before and after adding deformation at the grid points provided on the object 11 and calculates the displacement from the difference therebetween.

The displacement data storages 233b to 233d store in every sectional region the displacement data obtained at the displacement data measurement/calculation unit 233a in the former step.

The displacement curvature formula calculation unit 233e inputs the displacement data being stored in the displacement data storages 233b to 233d in every region. Assuming the object 11 with a rectangular shape and without the notches, the curvature formula calculation unit 233e calculates the displacement curvature formula to store the resultant data in the displacement curvature formula storage 233f.

The displacement calculation unit 233g calculates the displacement at a given position using the displacement curvature formula stored in the displacement curvature formula storage 233f.

Figure 21:
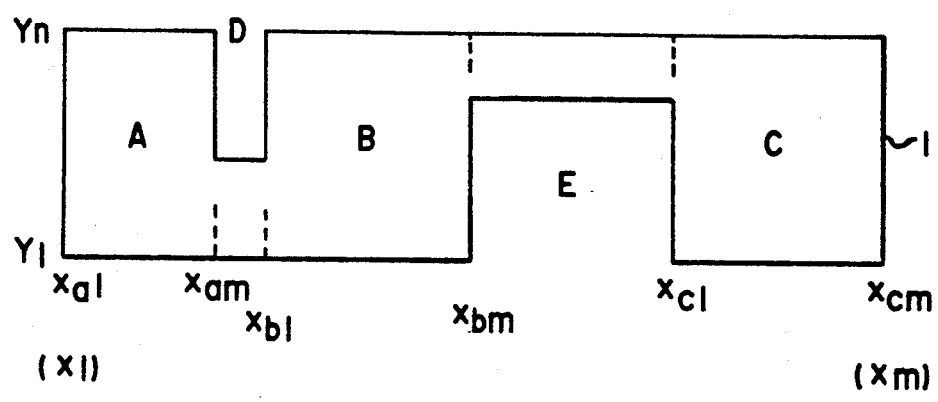
FIG. 21 is an illustration for explaining coordinates of the object to be measured.

FIG. 21 is an illustration for explaining coordinates of the object 11. Symbols D and E show the notches.

The object 11 is divided into rectangles A, B, and C to be mesh-cut.

In the region A, measuring points are defined as a position corresponding to a set element represented by a direct product "XA×Y" satisfying the following formula;

a set XA showing coordinate $x = [x_{a1}, x_{a2}, ---, x_{am}]$
a set Y showing coordinate $y = [y_1, y_2, ---, y_n]$ In the same way, in the region B, measuring points are defined as a position corresponding to a set element represented by a direct product "XB×Y" satisfying the following formula;

a set XB showing coordinate $x = [x_{b1}, x_{b2}, ---, x_{bm}]$
a set Y showing coordinate $y = [y_1, y_2, ---, y_n]$ Also in the same way, in the region B, measuring points are defined as a position corresponding to a set element represented by a direct product "XC×Y" satisfying the following formula;

a set XC showing coordinate $x = [x_{c1}, x_{c2}, ---, x_{cm}]$
a set Y showing coordinate $y = [y_1, y_2, ---, y_n]$ The measured displacement data in the regions A, B, and C are stored in the displacement data storages 233b to 233d, respectively as shown in FIG. 20. The displacement curvature formula calculation unit 233e assumes the object 11 with a rectangular shape and without the notches D and E, and obtains the displacement curvature formula "w" (x, y) which is considered as a displacement data at the position corresponding to a set element represented by a direct product "x×y" satisfying the following expression;

a set X showing coordinate $x = [x_1, x_2, --- x_m]$
a set Y showing coordinate $y = [y_1, y_2, ---, y_m]$ A domain of the displacement curvature formula "w" meets the following formula;

$[(x, y) | x_1 \leq x \leq x, y \leq y \leq y_n]$ where the notches D and E are included.

Conventionally, the displacement curvature formula has been obtained within only the region where the material body exists. According to the present invention, the displacement curvature formula is obtained, assuming a presence of imaginary body, even in the regions with the notches and without availability of measuring and obtaining the data. Thus, such processing becomes possible.

Figure 22:
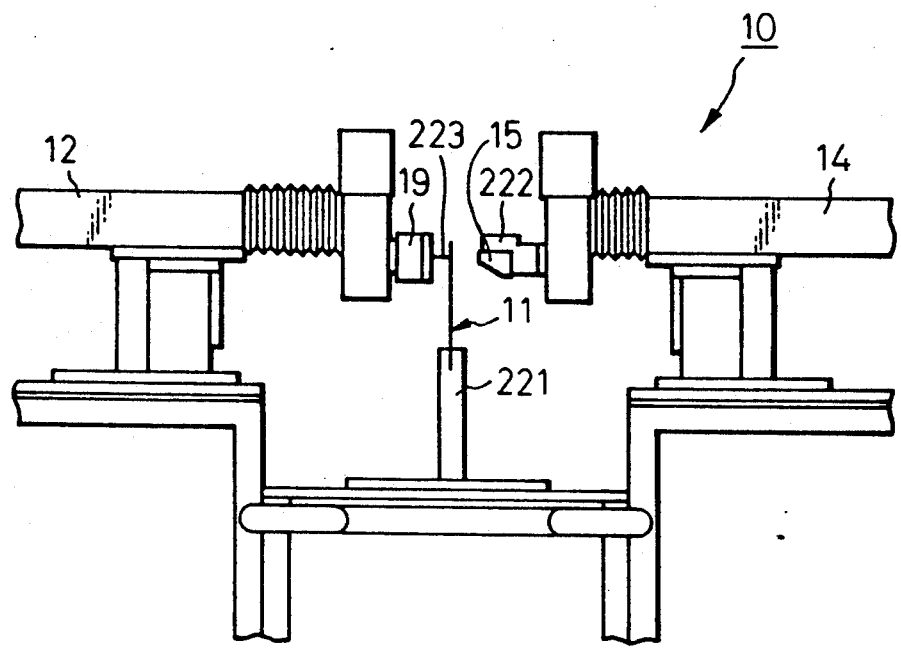
FIG. 22 is a structural view of a displacement measuring tool according to an embodiment of the present invention.

FIG. 22 is a structural view of a displacement measuring tool according to the present invention. Reference numerals 221 and 222 are mounting plates, and 223 is the pressing rod. The object to be measured, is supported vertically by the mounting plate 221. For measuring the displacement, the pressing robot 12 forces with a predetermined strength against the object 11 through the inner force sensor 13 and the pressing rod 223. The displacement gauge 15 mounted on the sensing robot 14 measures the displacement of the backside of the object 11, that is, the side without load thereon.

The advantages are obtained by measuring the backside displacement of the object using the measuring tool in the invention. The advantages are, ① the measurement around the pressing rod 223 becomes possible, and ② a reversed data different from the measurement of one side surface can be attained. Accordingly, the extension distortion otherwise the compression distortion can be measured.

Figure 23:
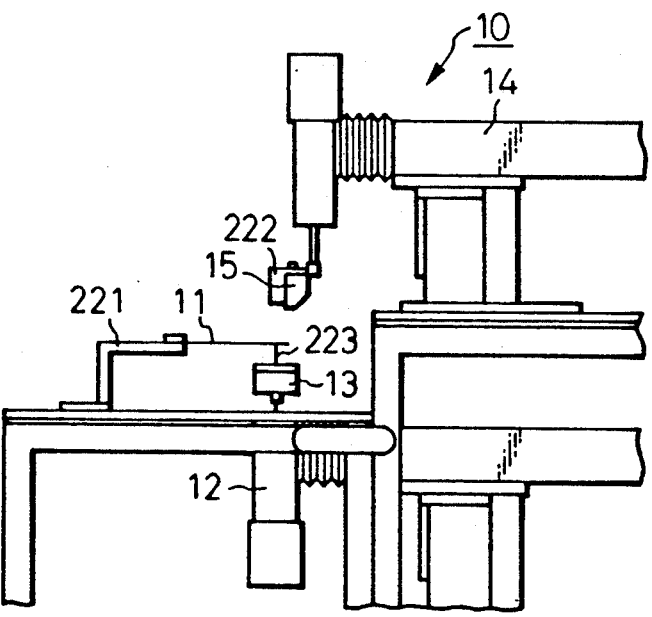
FIG. 23 is a construction view of a displacement measuring according to another embodiment of the present invention.

FIG. 23 is a structural view of a tool of the displacement measurement according to the invention. In this embodiment, the object 11 is mounted horizontally by the mounting plate 221. The inner force sensor 13 and the pressing rod 223 are mounted on the backside of the object 11. Although the advantages of this structure are the same as the above-mentioned embodiment, further advantage is obtained because the system can be made compact in size.

Figure 24:
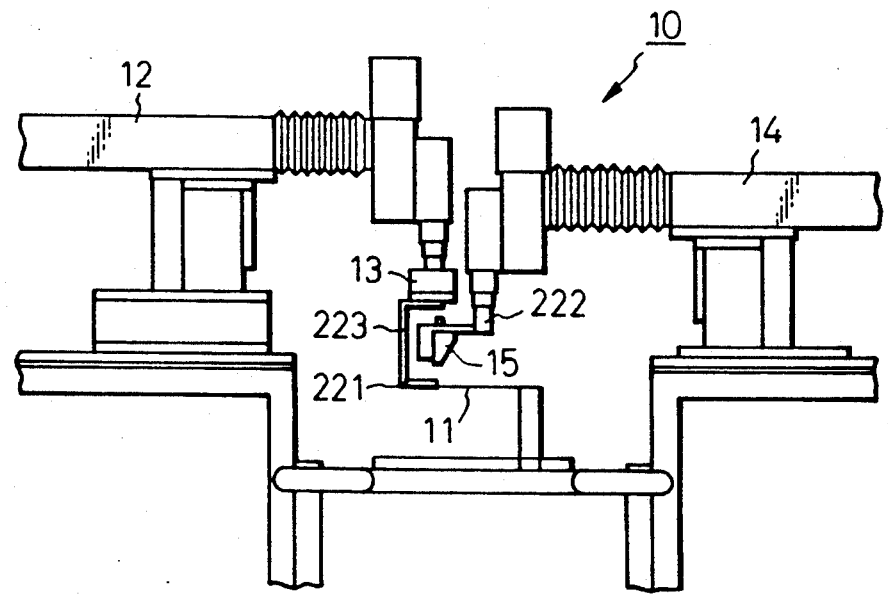
FIG. 24 is a construction view of a displacement measuring tool according to still another embodiment of the present invention.

FIG. 24 is a structural view of a displacement measuring tool according to another embodiment. The pressing rod 223 with U shape is mounted on the inner force sensor 13 as in the drawing. Conventionally, the head of the displacement gauge 15 often contacts with the pressing rod 223 to prevent the displacement measurement around the position pressed by the rod 223. According to the present invention, with such tool having U shape utilized, the head of the gauge 15 is prevented from contacting with the pressing rod 223, the measurement near the position pressed by the rod can thus be performed.

Figure 25:
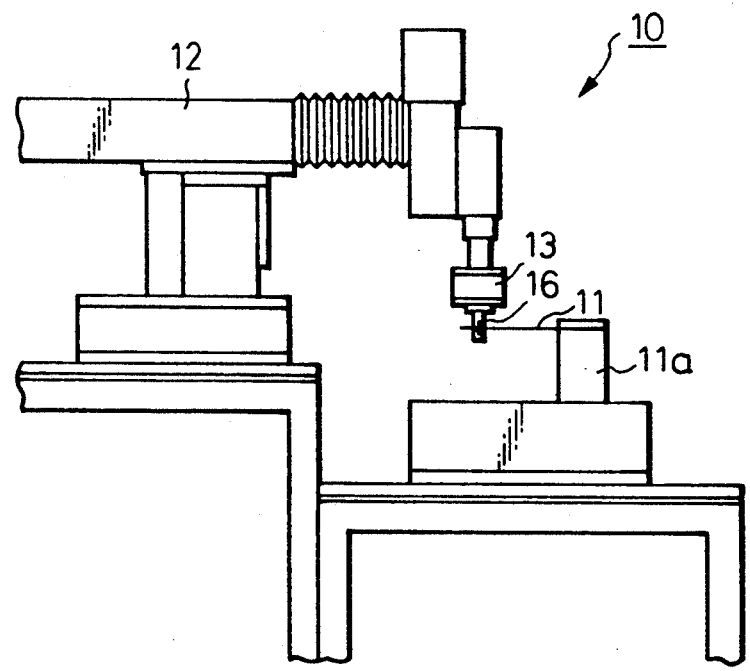
FIG. 25 is an illustration for explaining positioning of a holder of a bending fatigue test mechanism of a robot measuring system according to the present invention.
Figure 26A:
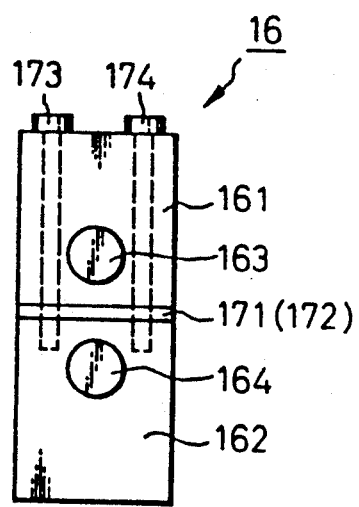
FIGS. 26A and 26B are side view and front views of the holder as shown in FIG. 25.
Figure 26B:
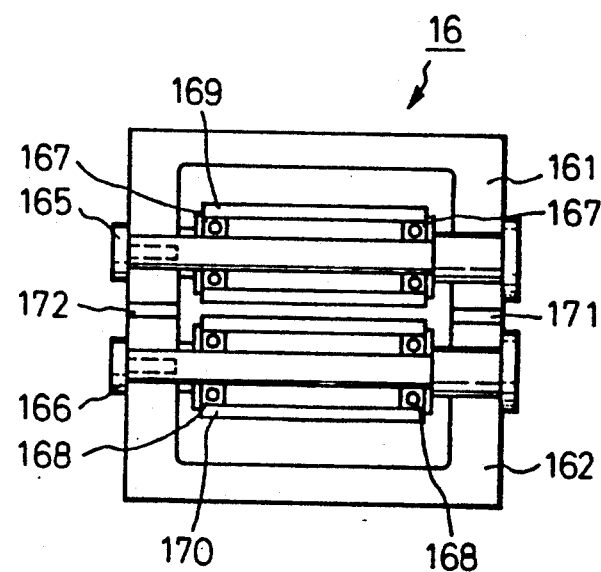
Figure 27:
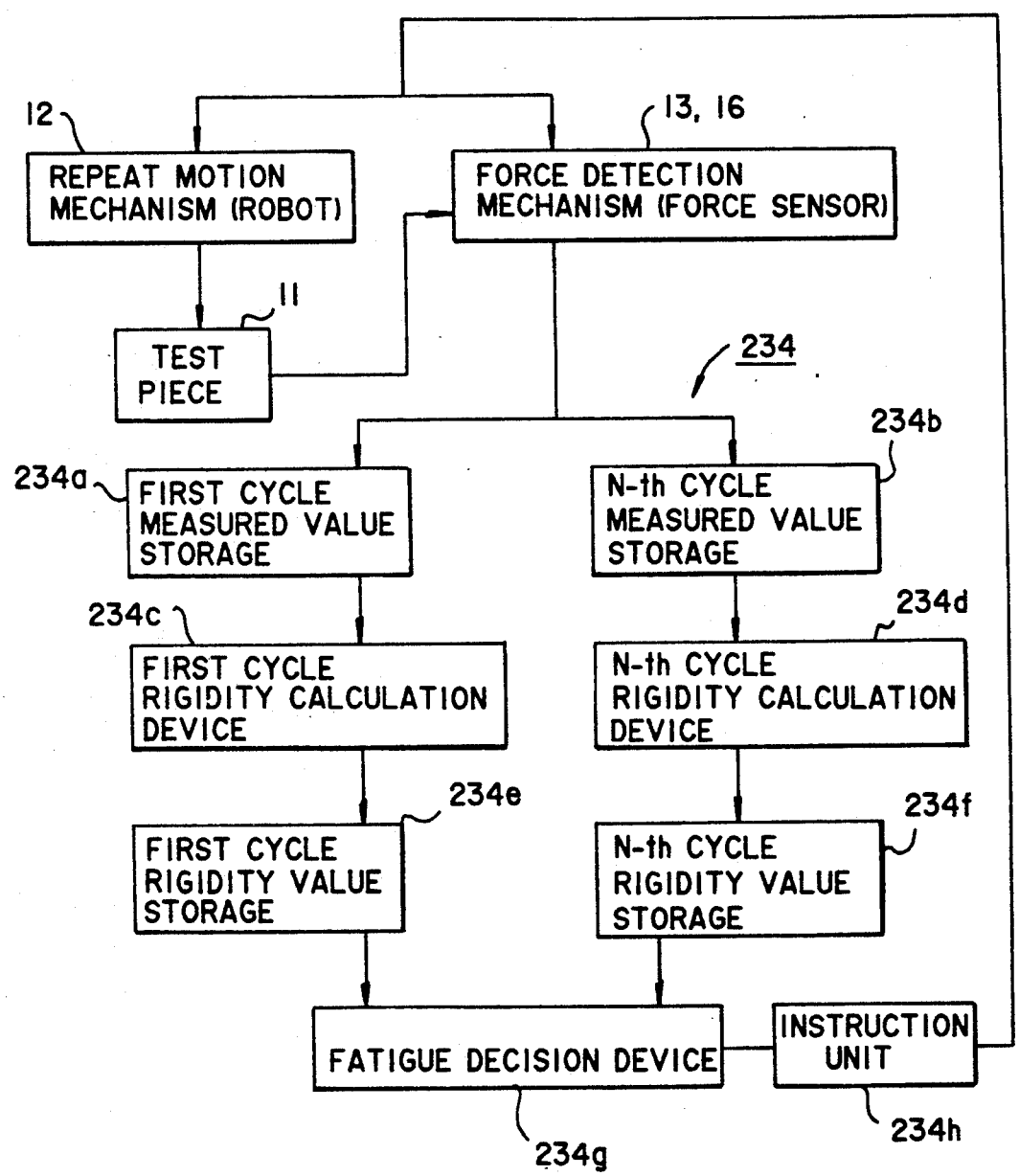
FIG. 27 is a block diagram of a bending fatigue test system according to an embodiment of the present invention.

FIG. 25 is an illustration of the mounting position of a holder of a bending fatigue test system. FIGS. 26A and 26B are a side view and a front view of the holder, respectively. FIG. 27 is a block diagram of a bending fatigue test system according to an embodiment of the present invention.

The block diagram of the bending fatigue test system shown in FIG. 27 corresponds to the bending fatigue test means 234 of the microprocessor 23. Referring to FIGS. 1 and 2, the inner force sensor 13 is provided in the pressing robot 12. The bending fatigue test system of the invention is provided on its inner force sensor 13 with the holder 16 for holding the object 11 as shown in FIGS. 25, 26A, and 26B. The holder 16 holds the other end (the side not fixed on the stationary part 11a) at the time of the bending fatigue test, and in this case the holder holds the test piece as movable in the orthogonal direction to the bending direction.

In the present invention, the object 11 is held so as to be movable in the orthogonal direction to the bending direction. Therefore, if the object 11 receives the force in the direction except for the orthogonal direction, it moves to the direction given by the force. Accordingly, the influence caused to the object 11 itself is extremely reduced.

The holder 16 is composed of, as shown in FIGS. 26A and 26B, housing 161 and 162 with U shape, inner shafts 163 and 164 passing in parallel each other through the housing 161 and 162, screws 165 and 166 connecting the inner shafts with the housing, bearings 167 and 168, outer shafts 169 and 170 supported by the bearings, spacers 171 and 172, and screws 173 and 174.

The object 11 to be measured is supported between the outer shafts 169 and 170. Due to this construction, even in the vertical movement of the holder 16, the position where the outer shafts 169 and 170 contact with the object 11, does not receive any appreciable friction force and can move automatically as a result of the free rotation of the outer shafts 169 and 170. Such structure above exhibits a largely higher performance comparing with the conventional structure in that, on receiving a bending force depending on a vertical movement of links, the test piece 11 suffers unwanted intensive force in the transverse direction.

An actual measurement contains two methods, one method is to add a predetermined force to the object 11, the other method is that the object 11 is moved a predetermined distance repeatedly. Referring to FIG. 27, latter method for measuring through the movement of the object 11 by a predetermined distance repeatedly, will be explained as follows.

Electric control devices of the bending fatigue test system 234 are included in the microprocessor 23 shown in FIG. 2. The pressing robot 12 acting the alternating motions is started by an instruction from the instruction unit 234$h$, and adds the alternating bending motions to the object 11. The instruction to the pressing robot 12 includes the number of times $N_0$ of bending and the distance of the movement. If the object 11 is determined to withstand without breaking, the alternating motions of $N_0$ times are terminated. However, the instruction can direct an infinitely repeated bending motions to the pressing robot 12, and then terminate the same by the instruction unit 234$h$ at the time of decision made by the data of fatigue degree of the object 11.

The inner force sensor 13 detects the pressing force added to the object 11. A resultant measured value of a first cycle is stored in a first cycle measured value storage 234$a$. An N-th cycle measured value is stored in an N-th cycle measured value storage 234$b$. A first rigidity calculation device 234$c$ calculates rigidity of the first cycle based on data of the first cycle measured value storage 234$a$ and stores the resultant data in a first cycle rigidity value storage 234$e$.

An N-th rigidity calculation device 234$d$ calculates rigidity of the N-th cycle based on data of an N-th cycle measured value storage 234$b$ and stores the resultant data in an N-th cycle rigidity value storage 234$f$.

A fatigue decision device 234$g$ is provided with a suitable data comparison means, so that the data of the first cycle rigidity value storage 234$e$ are compared with that of the N-th cycle rigidity value storage 234$f$. If the rigidity value of the N-th cycle becomes lower than a predetermined rate (for example, 60%) of that of the first cycle, the object 11 is judged as failure resulting from the fatigue. The decision result is given to the instruction unit 234h, which instructs the pressing robot 12 to terminate the measurement flow.

The instruction unit 234h instructs strength of the pressing force to the pressing robot 12 to produce a predetermined maximum output for the repeated motion on the object 11. If the object 11 breaks or moves over the predetermined distance, it is judged as fatigue.

As is explained in the aforegoing, the bending fatigue test system according to the present invention permits the holder of the object 11 to absorb the rotation in the horizontal and rotational directions. Accordingly, the force components except in the vertical direction giving vertical movement of the object 11 to be measured, are extremely reduced. As a consequence, the measurement condition becomes clear, and a higher measuring reliability can be obtained.

POSSIBILITY OF UTILIZATION IN INDUSTRIES

The robot measuring system according to the present invention is capable of automatically and quickly measuring the mechanical characteristics such as displacement, distortion of the plastic molded article and its distribution characteristics, accordingly, it can be utilized effectively for the structural designing of the body of the plastic molded article.

We claim:

1. A robot measuring system which automatically measures mechanical characteristics of an object to be measured when a bending load is applied to the object, the system comprising:
    a pressing robot for adding a predetermined pressing force to the object to be measured;
    force detection means, mounted to one end of a pressing rod, for detecting strength of the pressing force through the pressing rod;
    displacement detecting means for detecting a displacement of the object before and after the pressing force is applied thereto;
    a supporting robot for supporting the displacement detection means, and for moving the displacement detection means to a measuring position;
    a microprocessor for inputting resultant data of detection by the force detection means, for controlling a motion of the pressing robot based on the resultant data of detection, and for calculating various mechanical characteristics based on the detected resultant data input from the displacement detection means; and
    a memory for storing the various mechanical characteristics calculated by the microprocessor,
    wherein a calculation of the mechanical characteristics of a plastic molded article is performed by using a spline smoothing method on the resultant data.

2. A robot measuring system as claimed in claim 1, wherein said microprocessor comprises a distortion calculation means, curvature calculation means, displacement calculation means, and bending fatigue test means.

3. A robot measuring system as claimed in claim 2, wherein said distortion calculation means measures difference of shape appearing before and after deformation in said object, calculates a displacement distribution from the shape difference, calculates distortion of a neutral plane and a curvature component each of the object in accordance with the displacement distribution, and calculates a distortion distribution from a sum of the neutral plane distortion and the curvature component.

4. A robot measuring system as claimed in claim 3, wherein said displacement distribution is calculated by using said spline smoothing method on the resultant data of order three.

5. A robot measuring system as claimed in claim 3, wherein said curvature component is obtained by steps of,
    dividing a measurement region of the object into a plurality of regions based on a predetermined evaluation quantity,
    obtaining a sectional polynomial including an indeterminate coefficient approximating the displacement quantity of the object in every measurement region,
    attaining a evaluation function for evaluating an approximation degree produced by the sectional polynomial,
    determining said indeterminate coefficient based on a boundary condition between the evaluation function and a measured displacement quantity and between the regions, and
    re-dividing the measurement regions when said regions are not determined as suitable by means of such decision-making based on an evaluation quantity derived from the evaluation function.

6. A robot measuring system as claimed in claim 5, wherein said sectional polynomial is continuous at respective points.

7. A robot measuring system as claimed in claim 5, wherein a sum of square of difference between displacement quantity calculated from said sectional polynomial and displacement in every measuring point is obtained for all the measuring points.

8. A robot measuring system as claimed in claim 2, wherein said displacement calculation means comprises,
    a displacement data calculation unit for calculating a displacement data from difference value of shape measured before and after deformation in every grid point being set on said object;
    a displacement data storage for storing a displacement data obtained from the displacement data calculation unit into every divided region,
    a displacement curvature formula calculation unit for calculating a displacement curvature formula by inputting the stored displacement data to regard it as an object without notches,
    a displacement curvature formula storage for storing the displacement curvature formula, and
    a displacement quantity calculation unit for calculating displacement at positions designated using the stored displacement curvature formula,
    wherein, with a presence of the notches on the object, the displacement calculation means comprise steps of,
    dividing a plurality of regions so as to set grid shape measuring points on the object to be measured,
    inputting the displacement data measured, calculated, and stored in every sectional region,
    obtaining a displacement curvature formula regarding the object as without presence of the notches, and
    obtaining a displacement quantity at measuring points designated from said displacement curvature formula.

9. A robot measuring system as claimed in claim 8, wherein distortion is calculated at positions designated by performing a partial differential of second order of the displacement curvature formula.

10. A robot measuring system as claimed in claim 2, wherein said bending fatigue test means comprises:
 a first cycle measured value storage for storing a measured value of said first cycle of bending,
 an N-th cycle measured value storage for storing a measured value of said N-th cycle of bending,
 a first cycle rigidity calculation unit for calculating a first cycle rigidity in accordance with data of said first cycle measured value storage and storing in a first cycle rigidity value storage,
 an N-th cycle rigidity calculation unit for calculating an N-th cycle rigidity in accordance with data of said N-th cycle measured value storage and storing in an N-th cycle rigidity value storage,
 a fatigue decision unit having a comparison means and for determining as fatigue when said N-th cycle rigidity is not more than a predetermined rate of said first cycle rigidity by comparing said data of said first cycle rigidity value storage with that of said N-th cycle rigidity value storage,
 an instruction unit for receiving said decision result and outputting an instruction of end to said pressing robot to terminate said measurement.

11. A robot measuring system as claimed in claim 1, wherein said memory stores shape data at the time before and after occurrence of deformation, said shape data being one of a displacement distribution data, a neutral plane data, a curvature component data, a distortion distribution data, and a control program.

12. A robot measuring system as claimed in claim 1, wherein said force detection means is a force sensor.

13. A robot measuring system as claimed in claim 1, wherein said displacement detection means is a laser displacement gauge.

14. A robot measuring system as claimed in claim 1, wherein a target position of said supporting robot is given by adding product of a unit step quantity and a step coefficient onto an absolute reference position that is a movement reference of said supporting robot.

15. A robot measuring system as claimed in claim 14, wherein on the absence of designation of said step coefficient, said step coefficient is made as "1", and said target position is given by a sum of said reference position and said unit step quantity.

16. A robot measuring system as claimed in claim 14, wherein said target position is given by the reference position when only the reference position is designated.

17. A robot measuring system as claimed in claim 1, wherein a measuring tool is provided for mounting the object so that measurement is available for a mechanical characteristic of a surface reversed to said object surface receiving said pressing force from said pressing robot.

18. A robot measuring system as claimed in claim 1, wherein said pressing rod is provided with a space in measurement near a pressing position on the object so that the displacement detection means does not contact with the pressing rod.

19. A robot measuring system as claimed in claim 1, wherein in a bending fatigue test an end of said object is secured by a specified mounting plate, a holder is provided on a head of the force detection means for holding another end of said object movably in the orthogonal direction to the bending direction, and the pressing robot acts an alternating bend motion on the object through said holder.

* * * * *

UNITED STATES PATENT AND TRADEMARK OFFICE
CERTIFICATE OF CORRECTION

PATENT NO. : 5,156,053
DATED : October 20, 1992
INVENTOR(S) : SHIRAISHI et al

It is certified that error appears in the above-identified patent and that said Letters Patent is hereby corrected as shown below:

On the title page, Item [57] Abstract:

at column 2, line 9 from "force, a sensing" to --force. A sensing--.

Signed and Sealed this

Second Day of November, 1993

Attest:

BRUCE LEHMAN

*Attesting Officer*  *Commissioner of Patents and Trademarks*